US005639656A

United States Patent [19]
Wright, Jr.

[11] Patent Number: 5,639,656
[45] Date of Patent: Jun. 17, 1997

[54] ANTIBODIES REACTIVE WITH BIOLOGICAL MARKERS OF BENIGN PROSTATE HYPERPLASIA

[75] Inventor: George L. Wright, Jr., Va. Beach, Va.

[73] Assignee: Medical College of Hampton Road, Norfolk, Va.

[21] Appl. No.: 221,821

[22] Filed: Mar. 31, 1994

[51] Int. Cl.$^6$ .............................. C12N 5/12; C07K 16/28; A61K 51/10
[52] U.S. Cl. .................... 435/344.1; 530/388.2; 530/388.85; 530/389.1; 530/391.1; 530/391.3; 530/391.7; 435/332
[58] Field of Search .................... 530/387.3, 388.8, 530/388.85, 389.1, 389.7, 391.1, 391.3; 435/240.27

[56] References Cited

U.S. PATENT DOCUMENTS

Re. 33,405 10/1990 Chu et al. .
4,446,122 5/1984 Chu et al. .
4,863,851 9/1989 McEwan et al. .
5,153,118 10/1992 Wright, Jr. et al. .
5,227,471 7/1993 Wright, Jr. .

FOREIGN PATENT DOCUMENTS 0635575 1/1995 European Pat. Off. .

OTHER PUBLICATIONS

Muraro et al., Cancer Research, 1988, 48:4588.
Basta et al., "Cytokeratin Shedding in Urine: a Biological Marker for Bladder Cancer?," *British Journal of Urology*, 61:116–121, 1988.
Bostwick et al., "Prostatic Intra–Epithelial Neoplasia and Early Invasion in Prostate Cancer," *Cancer*, 59:788–794, 1987.
Brawer et al., "Keratin Immunoreactivity in the Benign and Neoplastic Human Prostate," *Cancer Research*, 45:3663–3667, 1985.
Edwards et al., "Proteins of Human Urine. II. Identification by Two-Dimensional Electrophoresis of a New Candidate Marker for Prostatic Cancer," *Clin. Chem.*, 28(1):160–163, 1982.
Merz et al., "Differential Expression of mRNAs Transporting Growth Factor β1 and β3 and C–POS in Human Normal Prostate, Benign Prostatic Hyperplasia and Prostatic Cancer, "*J. Urology*, 149 (4), Supplement, p. 472A, Abstract #1038, 1993.

Pagano et al., "Is There a Relationship between Benign Prostatic Hyperplasia and Prostatic Cancer?," *Eur. Urol.*, 20(suppl 2):31–35, 1991.
Partin et al., "Nuclear Matrix Protein Patterns in Human Benign Prostatic Hyperplasia and Prostate Cancer," *Cancer Research*, 53:744–746, 1993.
Starling et al., "Human Prostate Tissue Antigens Defined by Murine Monoclonal Antibodies," *Cancer Research*, 46:367–374, 1986.
Theyer et al., "Phenotypic Characterization of Infiltrating Leukocytes in Benign Prostatic Hyperplasia," *Laboratory Investigation*, 66(1):96–107, 1992.
Tsai et al., "Systematic Characterization of Human Prostatic Fluid Proteins with Two–Dimensional Electrophoresis," *Clin. Chem.*, 30(12):2026–2030, 1984.
Verhagen et al., "Colocalization of Basal and Luminal Cell–type Cytokeratins in Human Prostate Cancer," *Cancer Research*, 52:6182–6187, 1992.
Wright, Jr. et al., "Prostate Tumor–Specific Mucin–Like Antigen Differentiates Benign Prostate Hyperplasia From Well–Differentiated Prostate Adenocarcinoma," *J. Urology*, 145(4) Supplement, p. 295A, Abstract #329, 1991.
Wright, Jr. et al., "Differentiation of Benign Prostate Hyperplasia From Prostate Adenocarcinoma with Monoclonal Antibodies," *Proceedings of AACR*, 28, p. 349, Abstract #1384, 1987.
Wright, Jr. et al., "BP52: A Biomarker of Benign Prostate Hyperplasia," *J. Urology*, 151:297a, Abstract #279, 1994.
J.W. Goding, Monoclonal Antibodies: Principles and Practice, 1986, pp. 12, 78–85, 124–134, 282–287.
Wright et al., Int. J. Canc., 1991, 47:717.
Aguila et al., Immunotechnica, 1988, 2(2):1.

*Primary Examiner*—Christina Y. Chan
*Assistant Examiner*—Frank C. Eisenschenk
*Attorney, Agent, or Firm*—Arnold White & Durkee

[57] ABSTRACT

The invention provides compositions and methods for use in detecting benign prostate hyperplasia (BPH) and for differentiating BPH from normal prostate tissues and prostate cancer. Disclosed are monoclonal antibodies (MAbs) directed against a highly restricted biological marker of BPH, hybridoma cells secreting such MAbs and various methods for making and using BPH-specific antigens and antibodies, including methods and kits for the detection of BPH antigens and the diagnosis and therapy of BPH.

12 Claims, 2 Drawing Sheets

ANTIBODIES REACTIVE WITH BIOLOGICAL MARKERS OF BENIGN PROSTATE HYPERPLASIA

The government owns rights in the present invention pursuant to grant number CA26689 from the National Institutes of Health.

BACKGROUND OF THE INVENTION

1. Field of the Invention

The present invention relates generally to the fields of immunological compositions and detection methods. More particularly, it concerns compositions and methods for detecting benign prostate hyperplasia (BPH) and for differentiating BPH from normal prostate and prostate cancer. Disclosed are antibodies, including a monoclonal antibody, directed against a highly restricted biological marker of BPH, methods for making and using BPH-specific antibodies and antigens, and methods for the detection and diagnosis of BPH.

2. Description of the Related Art

Benign prostate hyperplasia (BPH) is the most common non-malignant proliferative abnormality found in any internal organ and the major cause of morbidity in the adult male. The initial development of BPH begins as early as 30 to 40 years of age and the prevalence is approximately 10% for that age group (Berry et al., 1984). With advancing age, the prevalence of BPH increases progressively. BPH occurs in over 75% of men over 50 years of age, reaching 88% prevalence by the ninth decade, often resulting in symptoms of outlet obstruction that can lead to bladder wall hypertrophy, increased risk of urinary infection, and chronic renal disease.

The currently accepted treatment for BPH is surgical resection of the prostate. The probability of requiring surgical intervention for BPH is approximately 25% if a man lives to 80 years of age. In the U.S. approximately 400,000 prostatectomies are performed annually to relieve urinary obstruction caused by this disease, making this the most common surgical procedure performed in U.S. males (Vital and Health Statistics, 1986; Carter & Coffey, 1990). The morbidity and mortality for transurethral resection of the prostate is 17% and 0.2–1.0%, respectively, including all age groups (Mebust et al., 1989). Surgical, hospitalization and other treatment for BPH are estimated to cost over a billion dollars per year. Although the statistics cited are for U.S. males, BPH has and continues to be a major health problem worldwide and will become even more significant as the aged male population increases.

The natural history of BPH is composed of two phases, a pathological phase and a clinical phase. Although almost every man who lives long enough will develop microscopic BPH, only about 50% will go on to develop macroscopic BPH, and only about 50% of the patients who develop macroscopic BPH will actually develop the clinical syndrome (Issacs, 1990). Thus, not all prostate growth requires clinical treatment. While prostate enlargement is a necessary condition of clinical BPH, size alone is usually not sufficient of itself to cause BPH to progress from the pathological to the clinical symptomatic phase. The clinician is thus faced with the problem of not being able to distinguish between pathological and clinical BPH.

Although evidently two separate diseases, recent observations have suggested a link between BPH and prostate cancer (CAP). For example, when BPH is found associated with small anterior CaPs, it has been reported that the cancer has generally originated within the hyperplastic nodules (McNeal et al., 1988). The early events for progression from either normal to BPH or normal to CaP have also been proposed to be similar (Partin et al., 1993). Nevertheless, the wide range of epithelial transformations that occur in both BPH and CaP, suggests that each end of this spectrum represents different disease processes that are not interrelated.

Due to the morbidity and mortality associated with BPH, the problem of overtreating, and the recent evidence that at least some BPH may be precursors of malignant changes in the prostate, it is evident that effective means for detecting BPH are urgently needed. Unfortunately, although a number of different molecules have been investigated in an attempt to find a specific or highly restricted marker for BPH, such a marker has yet to be identified.

Various markers allowing differentiation of the malignant phenotype from normal tissues have been identified, including prostate specific antigen (PSA), prostatic acid phosphatase (PAP) and prostate secretory protein (PSP). However, none of these substances have proven to be useful in the differentiation of BPH from CaP. Also, in contrast to BPH, monoclonal antibodies (MAbs) specific for CaP have been identified, including PD41 that recognizes a novel mucin (prostate mucin antigen, PMA) (Beckett et al., 1991); TURP-27, that recognizes a complex of 6–8 glycoproteins (Wright et al., 1991) and 7E11-C5 (Horoszewics et al., 1987) that recognizes a highly unstable complex of 3 glycoproteins.

It has been reported that the levels of certain growth factors, such as bFGF, EGF, PDGF or TGF-β, differ between BPH and CaP. Unfortunately, quantitative differences in the tissue concentrations of a particular molecule, unlike qualitative differences, would be unlikely to be specific enough to diagnose BPH or to differentiate BPH from CaP. Other studies have reported that BPH can be differentiated from CaP by the expression of basal cell cytokeratin (Verhagen et al., 1992; Sherwood et al., 1991; Brawer et al., 1985), however, a recent conflicting report showed that basal cell cytokeratin is also expressed by some prostate cancers (Verhagen et al., 1992). Furthermore, attempts to use cytokeratins to detect other cancers have been disappointing, such as the bladder cancer study that resulted in an unacceptably high frequency (55%) of false positives (AL-Hilaly et al., 1991). Another group proposed that the loss of HLA-DR may be a useful indicator of BPH progression to cancer (Theyer et al., 1992), but the variable expression of HLA-DR on benign ducts and epithelial cells will likely invalidate its use as a biomarker of BPH.

One- (1-D) and two-dimensional (2-D) gel electrophoresis has also been used in attempts to identify specific differences in the protein content of prostate tissue extracts and biological fluids from normal males and patients with prostate disease (Tsai et al., 1984; Johnson et al., 1985; Anderson et al., 1985; Carter et al., 1985; Wada et al., 1985; Gerhardt et al., 1985; Lee et al., 1986). These studies have yielded conflicting results, for example, one reported the presence of 5 protein spots unique to BPH (Anderson et al., 1985), whereas another showed no BPH-specific differences (Tsai et al., 1984). Furthermore, one proposed 40 kDa protein marker for prostate cancer identified by 2-D electrophoresis (Edwards et al., 1982), was later shown to be actin (Tsai et al., 1984).

It is thus evident that, despite intensive efforts in this area, the search for a unique or very specific marker for BPH has proven unsuccessful. The identification of a biological marker that allows BPH to be distinguished from normal or malignant tissues would represent a significant development, especially if such a marker could be readily detected using immunological techniques.

SUMMARY OF THE INVENTION

The present invention seeks to overcome these and other drawbacks inherent in the prior art by providing new compositions and methods for use in detecting BPH and in differentiating BPH from prostate cancer and normal prostate tissues. In certain aspects, the invention provides novel monoclonal antibodies (MAbs) directed against a highly restricted biological marker of BPH, hybridoma cells secreting such MAbs, methods for making and using such BPH-specific MAbs, for example, in the detection and purification of BPH antigens, and methods and kits for the clinical diagnosis and therapy of BPH. Various methods for obtaining further BPH-specific antigens, antibodies and biological compositions are also provided.

BPH-Specific Antibodies and Antigens

This invention provides BPH-specific, or BPH-restricted, antibodies and compositions containing such antibodies. A "BPH-specific or BPH-restricted antibody" is defined herein as an antibody that binds to BPH tissues, cells or antigens therefrom, but that shows little or no cross-reactivity with normal prostate or prostate cancer tissues, cells or antigens therefrom. A BPH-specific or BPH-restricted antibody may also be defined as an antibody that preferentially binds, or whose binding is generally restricted to, benign prostate antigens. These antibodies thus have substantial binding affinity for BPH antigens, but little or no binding affinity for normal or malignant prostate antigens.

The antigen recognized by BPH-specific antibodies will generally be an antigen that is present on, produced by, or generally associated with BPH tissues or cells, but that is not substantially present, produced by, or associated with normal or malignant prostate cancer tissues or cells. Such BPH-restricted antigens may be expressed, accessible to binding, or otherwise localized on the cell surfaces of benign prostate cells; antigens shed from, or secreted by, benign prostate cells, so that the antigens may appear in biological fluids such as seminal plasma, prostate fluid, urine or even serum; or the antigens may be simply associated with BPH tissues, for example, by being specifically bound to receptors or other molecules at the surface of BPH cells or otherwise preferentially adsorbed to such cell surfaces.

Alternatively, antigens recognized by BPH-specific antibodies may be proteins, polypeptides or other biomolecules that are associated with normal and/or malignant prostate tissues or cells, but which antigens are present in an altered form in BPH tissues. This "altered form" may take the form of being present in substantially larger quantities; of being present in a different sub-cellular compartment, particularly at the cell membrane; or of being mutated or otherwise altered so that a distinct epitope is formed, or revealed, which epitope is not substantially present on normal or malignant cells. Therefore, as used herein, the terms BPH-specific and BPH-restricted antigen are used for simplicity to encompass all the forms in which BPH tissues, and molecules therefrom, may be altered by the disease process so that they elicit a different immunological response.

As used herein, the terms "antibody" and "immunoglobulin" are used for simplicity to refer to all antibody-like or antibody-derived compounds that include one or more antigen binding regions and compositions containing such compounds. Antibodies in accordance with the invention may thus be polyclonal antibodies, as are present within blood, serum, plasma and fractions thereof, such as, e.g., an immunoglobulin fraction prepared by differential precipitation. Polyclonal antibody compositions may also be collectively termed "antisera". Also encompassed by the term antibodies are monoclonal antibodies, as may be present within ascites fluid, hybridoma culture supernatants, or MAbs further purified from such compositions.

Antibodies in accordance with this invention may also be any fragment or derivative of an antibody so long as this species functions to bind a BPH-specific or BPH-restricted antigen or epitope, i.e., the antibody fragment or derivative contains at least one antigen binding region (also termed complementarity determining region (CDR) or antigen combining site). Examples of such functional antibody fragments include, for example, single chain antibodies, Fv fragments, $F(ab')_2$ fragments and Fab fragments. Functional, antigen-binding antibody fragments may be constructed by a variety of means, such as, e.g., produced by restrictive chemical cleavage, enzymatic digestion or even using recombinant DNA technology.

The origin or derivation of a BPH-specific antibody or fragment thereof is not believed to be particularly crucial to the practice of the invention. Polyclonal antibodies and antisera may be obtained from virtually any experimental animal, such as a mouse, rabbit, rat, guinea pig, hamster, chicken, goat, and the like, or those obtained from a human subject, such as a patient with BPH. Where monoclonal antibodies are employed, they may be of murine, human, rat, monkey, hamster, chicken or even rabbit origin. Due to the ease of preparation and ready availability of reagents, murine monoclonal antibodies will often be preferred. Antibodies of various isotypes, such as IgG, IgM, IgA, IgE and even IgD, and all the various subtypes, and isotype switch variants, such as IgG and IgM combinations, are also included within the scope of the invention.

Still further examples of antibody and immunoglobulin compositions include chimeric antibodies in which domains from different origins are combined; humanized antibodies bearing human constant and/or variable region domains in combination with domains from mice, rats or other species. Humanized antibodies are preferred for use in certain in vivo embodiments as they are expected to have reduced immunogenicity. Various bispecific and trispecific antibodies in which at least one antigen combining region is directed against a BPH-specific or BPH-restricted antigen or epitope also fall within the scope of the invention. In addition to binding to a BPH-restricted antigen, such multi-specific antibodies may also bind to a wide range of other antigens, both on prostate tissues and other cells or tissues, including immunological effector cells.

The generation of antibodies directed against an antigen or antigens specific for, or restricted to, BPH has not been previously achieved due, in part, to the many similarities between normal, malignant and benign prostate cells and tissues. Disclosed herein are various means by which BPH-specific antibodies can be generated, including both methods involving first isolating a BPH-specific, or BPH-restricted, antigen and raising antibodies to such an antigen; and methods of directly generating a BPH-specific antibody by manipulating the immune system of an animal.

In other aspects, the present invention also concerns BPH specific or BPH-restricted antibodies obtainable by the methods described herein. One group of BPH-specific antibodies are those obtainable by isolating a protein, polypeptide or mutant form thereof, that is substantially expressed by BPH tissues or cells, but not normal or malignant prostate tissues or cells, and immunizing an animal with an amount of the protein or polypeptide effective to stimulate the production of BPH-specific antibodies.

A protein, polypeptide or antigen that is preferentially expressed by BPH tissues or cells, in comparison to normal and malignant prostate tissues or cells, may be isolated by a variety of methods, including both protein purification and molecular biological techniques. Thus, a protein, polypeptide or peptide unique or restricted to BPH tissues may be first identified by comparative protein separation techniques, and then obtained by subjecting larger quantities of BPH compositions or proteins to the same technique.

As antigens specific for different types of prostate tissues may be present on prostate cells, secreted by the cells, or both, both prostate tissue samples and biological fluid samples are appropriate starting compositions from which to identify and isolate specific proteins or polypeptides. Naturally, the choice of starting material will be influenced by the particular method employed and the desired goal. For instance, if it is desired to purify a secreted marker, or to generate an antibody against a secreted marker, one would employ biological fluids, such as, e.g. seminal plasma, prostate fluid, urine or even serum, as the starting materials for protein purification or antibody generation. However, the use of prostate tissue samples is considered to be generally appropriate for most applications concerning the identification of specific BPH biomarkers. Of course, in all instances, one would always employ a method capable of differentiating the BPH-specific proteins or antigenic elements from those elements that are common to all prostate cells.

In certain embodiments, the invention concerns BPH-specific antigens identifiable by 2-D gel electrophoresis and antibodies directed to such antigens. To identify a BPH-specific protein by 2-D gel electrophoresis, one would separately subject both a BPH composition and a normal/malignant prostate composition to 2-D gel electrophoresis under conditions effective to separate the constituent proteins and polypeptides. One would then compare the protein profiles generated, which would allow the identification of proteins or polypeptides that are unique to, or present at increased levels within, BPH tissues. Following identification, one could then obtain the unique protein by extracting, eluting or otherwise transferring the protein from the gel.

BPH-specific proteins and polypeptides may be isolated by molecular biological techniques, such as, e.g., subtractive hybridization cloning. In this technique, specific cDNA libraries are constructed from nucleic acid molecules isolated from normal, malignant and benign prostate tissues; the BPH-specific cDNA clones are then identified by subtracting the benign library from the normal and malignant libraries, or from a pooled library of both normal and malignant nucleic acid species. mRNAs preferentially expressed in BPH may then be isolated using reverse transcription and polymerase chain reaction (PCR) techniques. The invention thus also concerns BPH-specific antibodies obtainable by immunizing an animal with a protein expressed from an isolated BPH-specific nucleic molecule, and even BPH-specific antibodies obtainable by immunizing an animal with such a nucleic molecule itself (Tang et al., 1992; Cox et al., 1993; Fynan et al., 1993; Ulmer et al., 1993; Wang et al., 1993; Whitton et al., 1993).

Methods found by the inventor to be particularly suitable for generating BPH-specific antibodies are those methods involving an immunotolerizing/immunization protocol in which an animal is first rendered tolerant to an antigenic composition and is later immunized with a distinct composition, when antibodies are then generated only to unique antigens from the second composition. The present invention therefore encompasses antibodies that are generated by a method that involves first administering to an animal a composition containing prostate cancer and normal prostate antigens, under conditions effective to render the animal tolerant to the antigens in the composition, and then administering to the animal a second composition comprising BPH antigens, under conditions effective to elicit an immune response to unique antigens in the BPH composition, i.e., antigens that are newly-presented to the immune system.

In such immunotolerizing/immunization methods, suitable immunotolerizing conditions may include those such as drug-induced tolerance (e.g., using cyclophosphamide) and passive immunotolerance. The induction of neonatal tolerance to normal and malignant prostate antigens is a particularly preferred method of tolerizing an animal as there is generally less chance of tolerance being broken. Following tolerance induction, the BPH antigen-containing composition may be given to the animal under any standard immunizing condition, i.e., conditions effective to elicit an immune response that includes an antibody generative, i.e., B cell, response. The antibodies generated in response to the immunizing composition will, generally, contain BPH-specific antibodies.

Cross-Reactive Antibodies

Using the neonatal tolerance/BPH immunization method, the present inventor has developed a particularly useful BPH-specific monoclonal antibody, termed BP52. Thus, in certain embodiments, the invention concerns antibodies that bind to the BP52 antigen, i.e., those that are directed to, or have specific binding for affinity for, an antigen that is recognized by the monoclonal antibody termed BP52. The term "the BP52 antigen" refers to the antigen or antigens recognized by the BP52 antibody. These BP52 antigens or antigenic complexes are shown to be highly restricted to the ductal epithelium in BPH tissues. BP52 antibodies do not substantially bind to normal prostate tissues, or primary or metastatic prostate cancer tissues (CAP). Throughout the present text, the terms "recognizes" and "directed against" are used in an immunological context to refer to antibodies that have specific binding affinity for a given antigen or epitope.

In one particular embodiment, the invention is directed to monoclonal antibodies having the identifying characteristics of the murine monoclonal antibody secreted by hybridoma ATCC HB 11593. In a most preferred embodiment, the invention concerns the MAb termed BP52 itself and the hybridoma cell line, having ATCC Accession No. HB 11593, that produces this MAb.

However, the invention is by no means limited to the MAb BP52, rather it encompasses both BP52 and antibodies that are cross-reactive with BP52. An antibody that is "cross-reactive" with BP52, also termed "an anti-BP52 antibody", is an antibody, or a fragment or conjugate thereof, that is capable of competitively inhibiting, or cross-blocking, the binding of MAb BP52 to its BPH-restricted target antigen, antigens or antigenic complex (i.e., one that blocks binding to the BP52 antigen).

The identification of an antibody or antibodies that bind to the BP52 antigen is a fairly straightforward matter. This can be readily determined using any one of variety of immunological screening assays in which antibody competition can be assessed. For example, where the test antibodies to be examined are obtained from a different source to that of BP52, e.g., a rabbit, or are even of a different isotype, e.g., of an IgG isotype rather than IgM, simple competition assays may be employed in which BP52 and the test antibodies are premixed and then applied to an antigen composition. By "antigen composition" is meant any composition that contains the antigen or antigens recognized by BP52 in an accessible form, including tissue samples and various forms of purified or semi-purified antigens. Thus, protocols based upon immunohistochemical assays, ELISAs and Western blotting are suitable for use in such simple competition studies.

In such embodiments, one would pre-mix the BP52 antibodies with varying amounts of the test antibodies (e.g., 1:1, 1:10 and 1:100) for a period of time prior to applying to an antigen composition, such as a BPH prostate tissue section, an antigen-coated well of an ELISA plate or an antigen adsorbed to a membrane (as in dot blots and Western blots). By using specific secondary antibodies, e.g., anti-murine or anti-IgM secondary antibodies, one would be able to detect only the bound BP52 antibodies—the binding of which will be reduced below control levels by the presence of a cross-reactive test antibody that recognizes the same antigen as BP52.

To conduct an antibody competition study between BP52 and any test antibody, even another murine IgM MAb, one may first label BP52 with a detectable label, such as, e.g., biotin or an enzymatic, radioactive or florigenic label, to enable subsequent identification. In these cases, one would incubate the labelled BP52 antibodies with the test antibodies to be examined at various ratios (e.g., 1:1, 1:10 and 1:100) and, after a suitable period of time, one would then assay the reactivity of the labelled BP52 antibodies and compare this with a control value in which no potentially competing antibody (test) was included in the incubation.

The assay may be any one of a range of immunological assays based upon antibody binding and the BP52 antibodies would be detected by means of detecting their label, e.g., using streptavidin in the case of biotinylated antibodies or by using a chromogenic substrate in connection with an enzymatic label or by simply detecting a radioactive or fluorescent label. An antibody that binds to the same epitope as BP52 will be able to effectively compete for binding and thus will significantly reduce BP52 binding, as evidenced by a reduction in labelled antibody binding. In the present case, after mixing the labelled BP52 antibodies with the test antibodies, suitable assays to determine the remaining reactivity include, for example, immunohistochemical (e.g., immunoperoxidase) staining of tissue sections; ELISAs, RIAs, western blots or dot blots using BPH tissue extracts; immunoprecipitation of proteins from BPH tissue extracts; reactivity with BPH cell surface determinants assessed by FACS analysis. Immunoperoxidase (IP) staining of tissue sections and radioimmunoassays using tissue extracts are generally preferred, with immunoperoxidase staining, as described in Example IV, currently being the most preferred method.

In such competition assays, the reactivity of the labelled BP52 antibodies in the absence of any test antibody is the control high value. The control low value is obtained by incubating the BP52 antibodies with unlabelled antibodies of the same type, when competition would occur and reduce binding of the labelled antibodies. A significant reduction in labelled antibody reactivity in the presence of a test antibody is indicative of a test antibody that recognizes the same epitope, i.e., one that "cross-reacts" with the labelled antibody. A "significant reduction" in this aspect of the present application may be defined as a reproducible (i.e., consistently observed) reduction in binding of at least about 10–20% at a ratio of about 1:1, or at least about 20%–50 at a ratio of about 1:10, or more preferably, of equal to or greater than about 50%–90% at any ratio between about 1:1 and 1:100.

As with the BPH-specific antibodies defined above, antibodies that bind to the BP52 antigen recognized by the monoclonal antibody termed BP52 may be polyclonal antibodies, monoclonal antibodies, single chain antibodies, Fv fragments, F(ab')$_2$ fragments, Fab fragments, chimeric antibodies, humanized antibodies, bispecific antibodies, trispecific antibodies, a minimal reactive unit (MRU) or an antibody conjugate, so long as the antibody has at least one antigen combining region that has specific binding affinity for the BPH-restricted antigen recognized by BP52.

Hybridomas

In certain embodiments, the invention concerns hybridoma cells and cell lines which produce monoclonal antibodies that are capable of binding to the BP52 antigen. The hybridoma deposited with the ATCC having the designation ATCC HB 11593 is one particular example. However, the invention is not limited to this specific embodiment. Suitable methods for generating BPH-specific MAb-secreting hybridomas will be well known to those of skill in the art in light of the present disclosure and various publications, such as, e.g., The Cold Spring Harbor Manual for Hybridoma Development, incorporated herein by reference.

To obtain suitable hybridomas and MAbs in accordance herewith, one would initially immunize an experimental animal, preferably a mouse, in order to generate a BPH-specific antibody response, either using a specific antigen composition or using an effective immunotolerance/ immunization protocol. One would then obtain a population of spleen or other B cells from the animal. These cells would then be fused with cell lines, such as human or mouse myeloma strains, to produce antibody-secreting hybridomas which would be selected over the non-fused cells. The hybridomas would be isolated to obtain individual clones which would then be screened for production of antibody specific for BPH tissues, cells or antigens.

Hybridoma cell lines in accordance with the invention may also be employed as a source of nucleic acids (mRNA or DNA) encoding for the rearranged immunoglobulin genes that give rise to a particular MAb. The invention thus also encompasses nucleic acid molecules that encode an anti-BP52 antibody, and particularly, a nucleic acid molecule that encodes the MAb BP52. Such coding sequences may be isolated, cloned by recombinant DNA techniques and employed in recombinant expression protocols for the production of BPH-specific immunoglobulin chains. Using recombinant techniques, the precise specificity of the MAb may then be manipulated, as may be used to generate second generation antibodies with improved or otherwise altered binding capabilities, e.g., increased binding affinity or specificity. All such recombinant, engineered and second generation antibodies fall within the scope of the present invention.

Antibody Conjugates

A BPH-specific antibody of the invention, whether monoclonal or polyclonal, may also be linked to one or more other agents to form an antibody conjugate. One such example is the formation of a conjugate in which the antibody is linked to a detectable label. "Detectable labels" are compounds or elements that can be detected due to their specific functional properties, or chemical characteristics, the use of which allows the antibody to which they are attached to be detected, and further quantified if desired. Another such example is the formation of a conjugate comprising an antibody linked to a cytotoxic or anti-cellular agent, as are termed "immunotoxins".

Certain antibody conjugates may thus be used as diagnostic agents. Antibody diagnostics generally fall within two classes, those for use in in vitro diagnostics, such as in a variety of immunoassays, and those for use in vivo diagnostic protocols, generally known as "antibody-directed imaging".

Antibody conjugates for use in in vitro immunoassays, whether for diagnostic or scientific purposes, will generally be linked to a radiolabel, with $^{125}I$ being preferred; a fluorescent label, such as rhodamine or fluorescein isothiocyanate; a secondary binding ligand; or to an enzyme (an enzyme tag) that will generate a colored product upon contact with a chromogenic substrate. Examples of suitable enzymes include urease, alkaline phosphatase, hydrogen (horseradish) peroxidase and glucose oxidase. A preferred secondary binding ligand is biotin, which may be detected using an avidin or streptavidin compound. The use of such labels is well known to those of skill in the art in light and is described, for example, in U.S. Pat. Nos. 3,817,837; 3,850,752; 3,939,350; 3,996,345; 4,277,437; 4,275,149 and 4,366,241; each incorporated herein by reference.

Antibody conjugates or constructs for imaging will have the ability to provide an image of the benign tumor, for example, through magnetic resonance imaging, x-ray imaging, computerized emission tomography and the like. Diagnostic imaging antibody conjugates will thus generally be linked to nuclear magnetic spin resonance (paramagnetic) labels or radioactive labels. Many such imaging labels are known in the art, as are methods for their attachment to antibodies, e.g., U.S. Pat. Nos. 5,021,236 and 4,472,509, both incorporated herein by reference. Certain methods involve the use of a metal chelate complex employing, for example, an organic chelating agent such a DTPA attached to the antibody (U.S. Pat. No. 4,472,509).

In the case of paramagnetic ions, one might mention, by way of example, ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred. Ions useful in other contexts, such as X-ray imaging, include but are not limited to lanthanum (III), gold (III), lead (II), and especially bismuth (III).

Suitable radioactive isotopes for use in diagnostic applications include, for example, astatine$^{211}$, copper$^{67}$, galium$^{67}$, galium$^{68}$, indium$^{111}$, indium$^{113}$, iodine$^{123}$, iodine$^{125}$, iodine$^{131}$, mercury$^{197}$, mercury$^{203}$, rhenium$^{186}$, rhenium$^{188}$, rubidium$^{97}$, rubidium$^{103}$, technicium$^{99m}$ and yttrium$^{90}$. Technicium$^{99m}$ and indium$^{111}$ are generally preferred due to their low energy and suitability for long range detection.

Conjugates between a BPH-specific antibody and an anti-cellular agent, including both toxins and other pharmacologically active molecules, are also contemplated. As such, this invention concerns therapeutic conjugates, and pharmaceutical formulations thereof, in which a BPH-specific antibody or fragment, such as an anti-BP52 antibody, is linked to therapeutic agent. Particularly useful agents are considered to be toxins, such as ricin A chain; chemotherapeutic drugs, including antitumor drugs and antimetabolites; and most preferably, radioisotopes. Using such an antibody conjugate will allow agents such as these to be successfully targeted to a BPH cell, where they will then be internalized and will release the agent so that it exerts a specific biological effect on the BPH cells.

Immunological Detection

In general, both polyclonal and monoclonal antibodies against BPH-restricted antigens may be used in a variety of different ways. In particular embodiments, the antibodies may be employed in methods for detecting a BPH antigen or cell, as may be used in the purification of antigens and in the diagnosis of BPH.

Antigen detection methods may take the form of a variety of immunoassays, as are known to those of skill in the art and described in various publications, such as, e.g., Nakamura (1987), incorporated herein by reference. These methods generally comprise obtaining a biological sample suspected of containing a BPH antigen, such as a sample from a patient suspected of having BPH, and contacting the sample with a BPH-specific antibody under conditions effective to allow the formation of immune complexes. The immune complexes (primary immune complexes) are then detected, thus indicating the presence of a BPH antigen in the sample, as may be used to diagnose the patient from which the sample was obtained as having BPH.

The biological sample analyzed may be any sample that is suspected of containing a BPH-specific antigen, such as a prostate tissue section or specimen, a homogenized prostate tissue extract, a prostate cell, a prostate cell membrane preparation, separated or purified forms of any of the above prostate protein-containing compositions, or any biological fluid that comes into contact with prostate tissues, including seminal plasma, prostate fluid, urine and even serum. In preferred embodiments, it is contemplated that antibodies used in the detection methods will be those that bind to the BP52 antigen, as recognized by the monoclonal antibody BP52. In most cases, tissue samples or tissue extracts will be preferred. However, it is contemplated that fluid samples may also be employed in certain embodiments.

Contacting the chosen biological sample with the antibody under conditions effective to allow the formation of (primary) immune complexes is generally a matter of simply adding the antibody composition to the sample and incubating the mixture for a period of time sufficient to allow the antibodies to form immune complexes with, i.e., to bind to, any antigens present. After this time, the sample-antibody composition, such as a tissue section, ELISA plate, dot blot or western blot, will generally be washed to remove any non-specifically bound antibody species, allowing only those antibodies specifically bound within the immune complexes to be detected.

Methods for detecting primary immune complex formation are well known in the art and are generally based upon the detection of a label or marker, such as any of those radioactive, florigenic, biological or enzymatic labels outlined above. The anti-BPH antibody employed, such as BP52, or a BP52-like antibody, may itself be linked to a detectable label, wherein one would then simply detect this label, thereby allowing the amount of bound antibody and the amount of antigen present in the composition to be determined.

Alternatively, the bound anti-BPH antibody present within the primary immune complexes (primary antibody) may be detected by means of a second binding ligand that has binding affinity for the primary antibody and that is, generally, linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labelled secondary antibodies or ligands, and the remaining bound label is then detected.

Secondary antibodies for use in connection with the invention may be those directed against non-variable features, e.g., constant regions, of a BP52-like antibody. For example, as BP52 itself is a murine IgM antibody, one may employ a commercially available labeled anti-mouse IgM antibody as a secondary antibody. Secondary antibodies that have binding affinity for the primary BP52-like antibody may also be generated by immunizing an animal with a composition comprising the primary antibody, which antibodies may be subsequently labeled if desired. Unique secondary antibodies, whether labeled or unlabeled, that are directed against an antibody that binds the BP52 antigen are thus also encompassed by the present invention.

The immunological detection methods of the present invention may be employed in the diagnosis or monitoring of patients with BPH. In general, the detection of an antigen that reacts with a BPH-specific antibody, such as BP52, or an increase in the levels of such an antigen, in comparison to the levels in a corresponding biological sample from a normal subject or a patient with prostate cancer, is indicative of a patient with BPH. The basis for such diagnostic methods lies, in part, with the finding that BP52 was effective in identifying BPH and in differentiating the histopathologic types of prostate epithelial cells, i.e., benign from primary or metastatic tumors and normal prostate tissues. Also, BP52 did not show significant reactivity with life-sustaining normal tissues.

However, as is known to those of skill in the art, such a clinical diagnosis would not necessarily be made on the basis of this method in isolation. This is partly due to the fact that the BPH-restricted antibodies and antigens of the invention may not be absolutely specific in strictly chemical terms because, as is generally known in the art, biomolecules that are said to be specific often have a certain low level expression in other tissues, i.e., a limited cross-reactivity. A low level of cross-reactivity in a specific antigen is acceptable for use in clinical diagnostic methods, particularly where the method is used in conjunction with others.

Those of skill in the art are very familiar with differentiating between significant expression of a biomarker, which represents a positive identification, and low level or background expression of a biomarker. Indeed, background expression levels are often used to form a "cut-off" above which increased staining will be scored as significant or positive. Significant expression may be represented by high levels of antigens in tissues or within body fluids, or alternatively, by a high proportion of cells or ducts from within a tissue that each give a positive signal.

In terms of measuring the amount of signal that is indicative of BPH, the inventor has found that 100% of BPH tissues were positive for BP52 staining with 68–90% of BPH cells and ducts reacting with the BP52 MAb; whereas normal and malignant prostate epithelial cells and ducts showed occasional staining. By setting the positive cutoff at greater than about 5%, or at greater than about 10%, of the cells/ducts staining, the background staining is generally eliminated, allowing BPH to be readily differentiated from both normal and malignant prostate epithelia. Thus, staining of greater than about 5–10% of cells and ducts is the figure that is used herein to generally define an antigen that is present at increased levels in comparison to those in normal or prostate cancer tissues. For the most stringent definition, e.g., when using BP52 as a single diagnostic antibody, one may wish to establish the diagnostic cut-off as being of about 10% staining or greater.

The antibodies of the invention can thus also be used in combination with other known anti-prostate antibodies to provide additional information regarding the phenotype of normal or diseased prostate tissues. For example, BP52, or a related antibody, may be employed as one of a panel of antibodies for use in immunoassays. Various antibodies specific for markers of prostate cancer are known, such as, e.g., antibodies against PSA, PAP and PSP; and other specific antibodies, such as those designated P25, PD41, TURP-27 and 7E11-C5. U.S. Patents describing suitable CaP-specific antibodies include, U.S. Pat. Nos. 5,227,471; 5,153,118; 4,863,851; 4,446,122; and Re. 33,405, each incorporated herein by reference. The antibodies of this invention will be a valuable addition to the diagnostic panel as all the other antibodies identify normal or malignant cells or substantially cross-reactive markers thereof.

The present invention also provides methods for the in vivo diagnosis of BPH in a patient. Such methods generally comprise administering to a patient an effective amount of a BPH-specific antibody, such as BP52 or a like antibody that binds to the BP52 antigen, which antibody is conjugated to a marker that is detectable by non-invasive methods. The antibody-marker conjugate is allowed sufficient time to come into contact with reactive antigens that be present within the prostate tissues of the patient, and the patient is then exposed to a detection device to identify the detectable marker.

The types of detectable markers for use in such embodiments are those "imaging markers" described above. These include nuclear magnetic spin-resonance isotopes, such as gadolinium, that may be detected using a nuclear magnetic imaging device; and radioactive substances, such as technicium$^{99m}$ or indium$^{111}$, that may be detected using a gamma scintillation camera or detector. Dosages for imaging embodiments are generally dependent upon the age and weight of patient, however a one time dose of about 0.1 to about 20 mg, more preferably, about 1.0 to about 2.0 mg of Mab-conjugate per patient is contemplated to be useful.

In related embodiments, the invention concerns the preparation of immunodetection kits that may be employed in any of the foregoing or other immunodetection embodiments. Generally speaking, kits in accordance with the present invention will include, in a suitable container means, a BPH-restricted antibody, such as BP52 or an antibody that binds to the same antigen or antigens as BP52, together with an immunodetection reagent. The components of the kits may be packaged either in aqueous media or in lyophilized form.

The immunodetection reagent will typically comprise a label associated with the antibody, or associated with a secondary binding ligand, or antibody, that has binding affinity for the first antibody. As noted above, a number of exemplary labels are known in the art and any and all such labels may be employed in connection with the present invention. The kits may contain antibody-label conjugates either in fully conjugated form, in the form of intermediates, or as separate moieties to be conjugated by the user of the kit.

The container means will generally include at least one vial, test tube, flask, bottle, syringe or other container means, into which the antibody may be placed, and preferably suitably allocated. Where a second binding ligand is provided, the kit will also generally contain a second vial or other container into which this ligand or antibody may be placed. The kits of the present invention will also typically include a means for containing the vials in close confinement for commercial sale, such as, e.g., injection or blow-molded plastic containers into which the desired vials are retained.

The utility of the BPH-specific antibodies of the present invention is not limited to their diagnostic or clinical uses and they may be employed in a variety of different embodiments. For example, they may be employed in antibody cloning (expression cloning) protocols to obtain cDNAs or genes encoding BPH-restricted antigens, as described by Sambrook et al. (1989), incorporated herein by reference. A particularly useful application of such antibodies is their use in immunoabsorbent protocols to purify native or recombinant BPH-restricted antigens, for example, using an antibody affinity column. The operation of all such immunological and cloning techniques will be known to those of skill in the art in light of the present disclosure.

To purify a BPH-restricted antigen using an antibody of the invention, one would generally contact a BPH composition, such as a BPH tissue or cell extract, or even a biological fluid sample, with the antibody and obtain the antigen that specifically binds to the antibody after non-specifically bound species have been removed. Exemplary immunopurification techniques include immunoprecipitation and antibody affinity chromatography. In antibody affinity chromatography, the antibody is bound to a solid support, such as a column or bead, and exposed to a composition containing the antigen. Non-specifically bound components are then removed, e.g., by washing steps, and the bound antigen is then removed, or released, upon washing with a more stringent buffer.

The present invention also encompasses compositions that comprise a purified BPH-restricted antigen or antigens, as may be obtained using the specific antibodies. A preferred composition is one comprising the purified BP52 antigen, antigens or antigen complex, as obtained using an anti-BP52 antibody. A "purified BP52 antigen", as defined herein, is antigen that binds to the Mab BP52 and that has been purified to any degree relative to its natural state, i.e., purified away from other components of prostate tissues or fluids. A substantially purified BP52 antigen or antigen composition is one in which the BP52 reactive species forms one of the major components of the composition, such as constituting at least about 50% of the proteins in the composition.

The purified BP52 antigens of the invention may thus be compositions enriched with one or more BP52-reactive proteins, polypeptides or peptides, or may be in the form of a highly purified BP52 protein, polypeptide or peptide, purified from its natural source or obtained following cloning and recombinant expression. The term purified BP52 antigen also encompasses smaller polypeptides and peptides that include an epitope that is recognized by the Mab BP52, as may be obtained, for example, by peptide mapping.

The antibodies of the invention may also be used in inhibition studies to analyze the effects of BPH-restricted antigens in cells or animals. Anti-BPH antibodies, such as BP52, will also be useful in immunolocalization studies to analyze the distribution of the reactive antigens during various cellular events, for example, to determine the levels or cellular distribution of the antigen increase or change during disease development and/or progression.

Another, further potential use of the antibodies of the invention is in the treatment of BPH. Monoclonal antibodies are preferred for use in such therapeutic protocols, and more preferably, Mabs that are covalently attached to a toxic or anticellular compound, with MAbs that are conjuagted to a radioisotope being most preferred. As stated above, a variety of different types of substances can serve as the therapeutic agent, including radioactive isotopes, chemotherapeutic drugs and toxins, such as ricin A chain. Methods for preparing and using such therapeutic antibody-conjugates are known to those of skill in the art, as exemplified by U.S. Pat. Nos. 4,671,958, 4,741,900 and 4,867,973, incorporated herein by reference.

It is contemplated that the administration of a BPH-restricted antibody, or preferably, a therapeutic antibody-conjugate, to a patient will result in benign tumor cell killing and/or proliferation arrest. As such, another aspect of the invention concerns methods to treat BPH which generally comprise administering to a patient pharmaceutically acceptable composition comprising a therapeutically effective amount of an antibody or antibody-conjugate in accordance with those disclosed herein. A preferred conjugate for use in therapeutic regimens is a conjugate comprising an anti-BP52 antibody linked to a radioisotope. The formulation of antibodies in suitable forms for administration to a human subject will be known to those of skill in the art in light of the present disclosure and various published references, such as, e.g., Remington's Pharmaceutical Sciences, 16th Ed. Mack Publishing Company, 1980, incorporated herein by reference.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE PREFERRED EMBODIMENTS

A. Benign Prostate Hyperplasia, BPH

Figure 1:
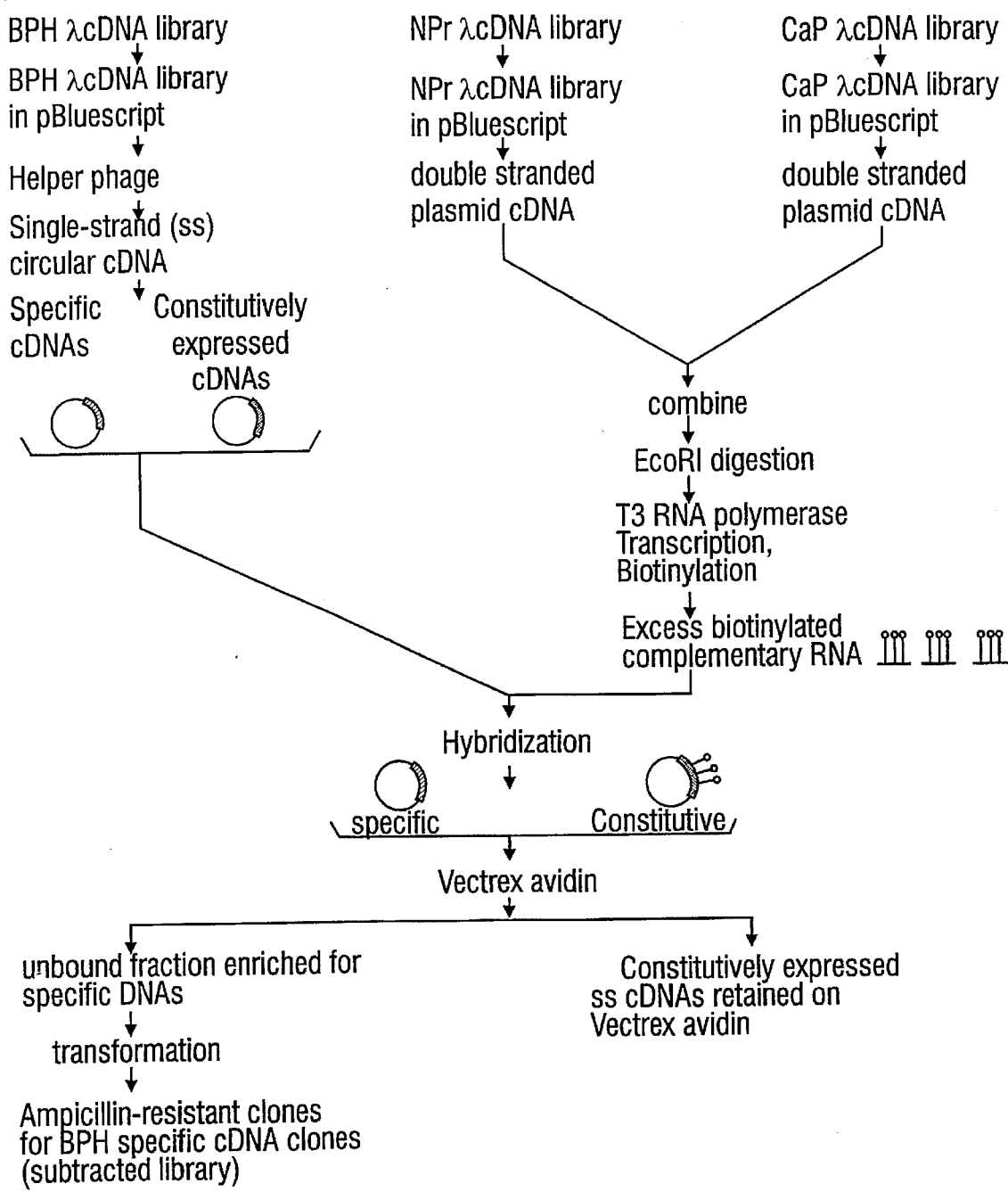
FIG. 1 Schematic outline of cloning procedure for construction of subtracted library enriched for sequences expressed in benign prostate hyperplasia (BPH).

Approximately 75% of men over 50 years of age have benign prostate hyperplasia (BPH) and, therefore, are at increased risk for bladder wall hypertrophy, urinary infection and chronic renal disease. The currently accepted treatment for BPH is surgical resection of the prostate, with the probability of requiring surgical intervention for BPH being approximately 25% if a man lives to 80 years of age. In 1986 alone, BPH surgery was reported to be the second leading cost of Medicare reimbursements for a surgical procedure in the U.S. (Carter & Coffey, 1990; Bureau of Data Management and Strategy, 1988). BPH is, of course, also a significant health problem in countries other than the U.S.

Not all prostate growth requires clinical treatment. However, as size alone is not generally sufficient to indicate progression to symptomatic disease, this makes the decision of whether to operate a difficult one. This leads to over treatment, and increased morbidity and mortality from surgery. It also is true that the successful treatment for clinical symptoms, i.e. transurethral incision of the prostate, balloon dilation, stints, and medical therapy, does not necessarily require elimination of pathological BPH (Issacs, 1990; Bosch, 1991).

Until recently, BPH and prostate cancer were considered to be two separate diseases. Current observations suggest a link between BPH and prostate cancer. It is now universally accepted that prostate hyperplasia/hypertrophy (benign or malignant) is mediated by 5-alpha-dihydrotestosterone. In the absence of this enzyme, neither BPH or CaP have occurred. Furthermore, quite often the simultaneous presence of benign and malignant disease is observed. McNeal et al. (McNeal, 1988) observed that when BPH was found associated with small anterior CaPs, the cancer had originated within the hyperplastic nodules, and suggested that one half of anterior CaPs may represent a malignant transformation of BPH tissue. Nevertheless, the wide range of epithelial transformations that occur in both BPH and CaP, suggests that each end of this spectrum represents different disease processes that are not interrelated. Intermediate histologic lesions such as atypical adenomatous hyperplasia (AAH) and prostatic intraepithelial neoplasia (PIN) may be interpreted as a link between BPH and PC, i.e. BPH>(AAH) (PIN)>CaP (Pagano et al., 1991; Bostwick & Brawer, 1987). A recent report by Partin et al. (Partin et al., 1993) comparing the nuclear matrix protein patterns in BPH and prostate cancer provides additional evidence that the early events for progression from either normal to BPH or normal to prostate cancer are similar.

The high cost of healthcare, the problem of overtreating, and the recent evidence that at least some BPH may be precursors of malignant changes in the prostate suggest that a BPH biomarker is needed to (Berry et al., 1984) detect the (age of) onset of BPH, (Vital and Health Statistics, 1986) predict and monitor progression, (Carter & Coffey, 1990) monitor effectiveness of medical therapy, especially for new hormone therapies, and (Mebust et al., 1989) differentiate benign from malignant prostate disease.

A study of the scientific literature reveals that little progress has been made in the search to identify a specific or highly restricted biomarker of BPH. A number of different cellular molecules have been identified and measured in prostate tissues in an attempt to understand the mechanisms of prostate growth and the multifaceted etiology of this complex disease. Growth factors such as bFGF, EGF, PDGF, and TGF-beta, and various enzymes and receptors have been described (Ibrahim et al., 1993; Mellon et al., 1992; Nakamoto et al., 1992; Sherwood et al., 1992; Yang et al., 1992; Stearns & Wang, 1993; Matzkin & Soloway, 1992; Lawson, 1990; Fiorelli et al., 1991; Mori et al., 1990; Shalkh et al., 1990; Maygarden et al., 1992; Graham et al., 1992; Kumar et al., 1990; Abrahamsson et al., 1988; Rackley et al., 1991; O'Brien & Lynch, 1988; Lloyd et al., 1992). Most of the changes observed with these molecules between BPH and CaP are quantitative differences in tissue concentrations rather than a qualitative difference. Although it remains to be determined whether any of these molecules could be used for the diagnosis and/or monitoring of prostate disease progression, it seems highly unlikely that these molecules could be used to diagnose BPH or to differentiate BPH from CaP. Other molecules, such as PSA, PAP, PSP and calcitonin, have been evaluated in urine, serum, and seminal plasma (Lilja & Abrahamsson, 1988; Abrahamsson et al., 1988; Teni et al., 1988; van-Dieijen-Visser et al., 1988; Shah et al., 1992; Frenette et al., 1991; Lokeshwar & Block, 1992; Uchijima et al., 1991; Tremblay et al., 1987; DeVere et al., 1992; Dalton, 1989). Again none of these substances were useful markers to differentiate BPH from CaP.

With the exception of the growth factor studies, most of the investigations have focused on markers or changes that identify the malignant phenotype. The two cellular components that have showed considerable specificity are cytokeratins and HLA-DR and several studies have reported that BPH can be differentiated from CaP by differential expression of cytokeratins (Verhagen et al., 1992; Sherwood et al., 1991; Brawer et al., 1985). Basal cell cytokeratin is found only in basal cells of normal, BPH and early stage PIN lesions. A recent report, however, showed that basal cell cytokeratin can be expressed by some prostate cancers (Verhagen et al., 1992). Even if basal cell cytokeratin could be measured in body fluids, it is not likely to be useful to differentiate normal from BPH prostate growth. For example, measurement of cytokeratins in urine from patients with bladder cancer using an antibody raised against cytokeratin extracted from bladder carcinoma cells resulted in a high frequency (55%) of false positive results (AL-Hilaly et al., 1991).

Another observation was recently reported by a group of investigators when identifying the infiltrating cells in BPH tissues (Theyer et al., 1992). They found that the HLA-DR molecule was expressed on 40% (mean) of benign ducts, rarely expressed on normal epithelial cells and not expressed on malignant prostate cells. This "cross-reactivity" is an interesting observation, and if confirmed, the loss of HLA-DR may be a useful BPH marker of progression to cancer. However, the variable expression of HLA-DR on benign ducts and epithelial cells will likely invalidate its use as a biomarker of BPH.

Several groups of investigators have used one- (1-D) and two-dimensional (2-D) electrophoresis to separate and characterize the proteins in human prostate tissue extracts and in prostate fluid, seminal plasma and urine from normal males and patients with prostate disease (Lee et al., 1986; Johnson et al., 1985; Tsai et al., 1984; Edwards et al., 1981; Edwards et al., 1982; Anderson et al., 1985; Grayhack et al., 1979; Carter et al., 1985; Wada et al., 1985; Gerhardt et al., 1985). These initial studies demonstrated that protein alterations, i.e., presence, absence or changes in concentration, could be identified by 2-D electrophoresis. Anderson et al. (Anderson et al., 1985) reported protein spots unique to each tissue type, and 5 protein spots were said to be detected only in BPH. In another study, no alterations were observed in prostatic fluid samples from patients with BPH, although several proteins were significantly absent in prostatic fluid from cancer patients, and one was absent from fluid of patients with both prostatitis and BPH (Tsai et al., 1984).

Another study described the identification of a candidate protein marker (PCA-1) for prostate cancer in urine by 2-D electrophoresis (Edwards et al., 1982). Tsai et al. (Tsai et al., 1984) identified this 40 kDa protein in prostatic fluid as belonging to actin, and this is not, therefore, a specific marker for prostate cancer. Partin et al. recently reported that nuclear matrix protein spots differ between normal prostate, BPH, and prostate cancer (Partin et al., 1993). Some spots were found only in normal prostate or prostate cancer, while others were found common to normal prostate and BPH or BPH and prostate cancer. It is significant though, that none were found unique to BPH. Thus, although all these studies concluded that 2-D electrophoresis was a powerful technique to detect potential markers of disease in prostate fluid, seminal plasma and urine, follow-up studies do not yet appear to have yielded any positive results.

B. Strategies to Identify Specific Markers for BPH

In antibody generation following immunization, there is a strong bias in favor of generating antibodies to a few immunodominant antigens because of the overwhelming antigenemia and antigenic competition (Radovich & Talnage, 1967). Not surprisingly, the inventor failed to produce specific BPH antibodies using standard immunization protocols, most likely due to this antigenic competition problem. The inventor thus reasoned that methods to overcome this phenomenon would be important in raising specific antibodies against BPH cells, particularly as these cells retain much of the differentiated phenotype of their tissue of origin so that BPH-specific antigens represent a very small minority of the total antigens. Prior enrichment of the immunogens, for example, using 2-D electrophoresis (as described in Example VII), is one way of enhancing the chances of successfully obtaining antibodies that recognize a unique BPH protein.

B1. Depletion of Irrelevant Antigens from Polyclonal Antisera

Another way of promoting the generation of BPH-specific antibodies is to deplete polyclonal antisera of unwanted antigens and to identify the unique antigens by Western blotting. For this, polyclonal antisera was generated against pooled seminal plasma obtained from CaP or BPH patients. Four adult Balb/c mice were immunized four times over a period of 22 days with 50–200 g of protein; on day 28 the mice were sacrificed and blood obtained. The pooled polyclonal antiserum was adsorbed with 5 ml of adsorption antigen (1 mg/ml of normal or BPH or CaP seminal plasma or tissue extract) at 4° C. overnight. The precipitate (ag-ab complex) was removed by centrifugation (12,000× g) at 4° C. for 1 hour. This process was repeated two times.

The antibody not removed by adsorption served as the primary antibody used to detect unique antigens by Western blotting. Any unique proteins (antigens) identified in this manner could then be electroeluted from a gel and used as immunogens for production of monoclonal antibodies. The following combinations of antigen reduction studies were conducted by the inventor: CaP antisera adsorbed with normal seminal plasma; CaP antisera adsorbed with BPH seminal plasma; BPH antisera adsorbed with CaP seminal plasma; BPH antisera adsorbed with normal seminal plasma; and BPH antisera adsorbed with BPH tissue extract. Unfortunately, none of these combinations resulted in the identification of proteins unique to BPH seminal plasma. This may have been due to incomplete pelleting of the Ag-Ab complex, whereby the antibody was eventually released from the antigen and then free to react against the common antigens, as detected by Western blotting.

B2. Drug-Induced Tolerance

Another approach contemplated by the inventor involved manipulating the mouse immune system so that it preferentially responded to the minor, but tissue specific, antigens. There are three such approaches that have been designed to eliminate lymphocyte populations specific for irrelevant antigens: (Berry et al., 1984) drug-induced immune suppression, (Vital and Health Statistics, 1986) neonatal tolerance induction, both of which are "active" forms of tolerance induction, and (Carter & Coffey, 1990) "passive" tolerance.

Immune suppression based on the use of an agent, such as the alkylating agent cyclophosphamide, which is toxic for stimulated lymphocytes is sometimes referred to as "drug-induced tolerance." Sequential immunization with irrelevant immunogens and subsequent cyclophosphamide injection is supposed to eliminate the immune response against these components, even if they are present in later immunogen mixtures.

For this approach, groups of three Balb/c mice, 6–8 weeks old, were inoculated according to a basic immunotolerizing/immunizing protocol. Two mice served as the test mice, receiving the tolerogen and cyclophosphamide doses, while one mouse served as the control, receiving the tolerogen and immunogen doses but no cyclophosphamide. For the basic protocol, tolerizing doses of 100 g of protein (tolerogen) were injected intraperitoneally (IP) 35 on days 0 and 14. Each tolerizing dose was followed by a 200 mg/kg dose of cyclophosphamide IP at 10 minutes, 24 and 48 hours. The same mice were then immunized, IP, on days 28 and 38 with 100 g of protein (immunogen) mixed with an equal volume of Ribi adjuvant. The final boost of 100 g of immunogen (without adjuvant) was administered as a 50 g injection intravenously and 50 g IP on day 48. Three days later, on day 51, the spleens were removed aseptically and fused with the parent myeloma cell line NS-1 according to standard fusion protocol.

Serum was obtained by tail bleed periodically during the study from each of the test and control mice and titered for reactivity against the tolerogen and immunogen proteins using pre-immune serum as a control. Using a solid phase indirect microtiter immunoassay (ELISA), and indirect immunoperoxidase assay of tissue specimens, the progress and completeness of the tolerization/immunization process was monitored.

Both prostate tissue extracts and seminal plasma contain a large number of serum proteins in high concentration that can easily overwhelm the mouse immune system, such that tolerance to minor common antigens is not effective. To enhance efforts to induce immune responses against immunogens of interest, the inventor immunodepleted crude tissue extracts or seminal plasma fractions of serum proteins by biospecific affinity chromatography. For the first immunodepletion study, polyclonal anti-human serum proteins and anti-human albumin were separately coupled to CNBr-activated Sepharose 4B by the reductive amination of NaCNBH4. Seventy-five to 90% coupling efficiency was obtained at concentrations of 10–20 mg protein/ml gel bed. One- and two-dimensional gel electrophoresis showed that the immunodepleted fractions of human serum or seminal plasma contained no serum proteins (after one or two passes over the affinity column). With this approach, it was determined that up to 87% of normal seminal plasma consists of albumin and other serum proteins.

The following drug tolerance/immunization studies have been conducted or are in progress: PD CaP tissue extract as a tolerizing agent and BPH (glandular) tissue extract as an immunizing agent; PD CaP tissue extract as a tolerizing agent and BPH (glandular) immunodepleted tissue extract as an immunizing agent; normal prostate extract as a tolerizing agent and BPH (glandular) immunodepleted tissue extract as an immunizing agent; WD/MD (well- to moderately-differentiated) CaP tissue extract as a tolerizing agent and BPH (glandular & stromal tissue extract) as an immunizing agent; and CaP seminal plasma pool as a tolerizing agent and BPH seminal plasma pool as an immunizing agent.

These studies are generally at the stage of either establishing hybridomas or screening culture supernatants for specific antibody reactivity. The hybridoma culture supernatants are screened at the 96 well stage against both the immunogen and tolerogen by ELISA. The positive clones are transferred to 48 well plates, then to 24 well plates where they are screened again by ELISA and also by immunoperoxidase staining against the immunizing and tolerizing tissues. The positive hybridomas are then double cloned and isotyped. The monoclonal antibodies of highest specificity will be subjected to extensive screening using a variety of normal and malignant tissues, cell lines and seminal plasma.

One disadvantage of this method is due to the transient effect (approx. 4 weeks) of immune suppression, which hampers induction of a strong secondary immune response against relevant immunogens. This "break" in immunosuppression likely explains the failure of the inventor to develop BPH-specific antibodies using the drug-induced tolerance methods described above.

B3. Passive Tolerance Induction

The term "passive tolerance" refers to the process by which tolerance is induced by coadministering serum antibodies from mice immunized with irrelevant immunogens along with the immunizing dose of relevant immunogens. By passive immunization against the dominant irrelevant antigens the reaction against these antigens is suppressed, and simultaneous active immunization with relevant antigens allows the immune system to effectively respond to the tissue specific immunogens. Thus, in the present strategy, antisera raised against CaP protein-containing compositions would be given at the same time as the BPH protein immunogens themselves.

Unfortunately, passive tolerance studies have also failed to yield BPH-specific antibodies, which may be due certain conditions, such as the age of mice, time of tolerance induction, and the like, not being optimized.

B4. Neonatal Tolerance Induction

The inventor reasoned that many of the problems with drug-induced and passive tolerance induction could be circumvented by manipulating the neonatal immune system. Neonatal tolerance induction involves the endogenous elimination of lymphocyte populations specific for self antigens during a critical postnatal period of mouse development. Irrelevant immunogens are injected during this period (i.e., 1 or 2 day old mice) and a mixture of relevant and irrelevant immunogens are given at later stages (i.e., 6–8 weeks).

The present inventor has successfully employed neonatal tolerance induction to identify and isolate a clone secreting a MAb, termed BP52, that preferentially recognizes an antigen expressed by BPH epithelial cells.

Studies to date have shown that BP52 stains ducts in 24/27 (89%) BPH specimens examined, with staining of BPH ducts ranging from 20% to 90% (mean 72%). Similar results were obtained using a radioimmunoassay to detect the BP52 antigen in tissue extracts. BP52 also recognizes less than 3%, and about 10%, of the ductal epithelial cells or tumor cells stained in normal prostate tissues and CaP tissues, respectively. BP52 is thus proposed for use as a highly restricted biomarker for BPH detection and differentiation from CaP, particularly in immunohistopathological analyses of tissue sections.

C. Monoclonal Antibody Generation

Means for preparing and characterizing antibodies are well known in the art (See, e.g., Antibodies: A Laboratory Manual, E. Howell and D. Lane, Eds., Cold Spring Harbor Laboratory, 1988, incorporated herein by reference).

The methods for generating monoclonal antibodies (MAbs) generally begin along the same lines as those for preparing polyclonal antibodies. Briefly, a polyclonal antibody is prepared by immunizing an animal with an immunogenic composition in accordance with the present invention (either with or without prior immunotolerizing, depending on the antigen composition and protocol being employed) and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed Mycobacterium tuberculosis), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, may also be given. The process of boosting and titering is repeated until a suitable titer is achieved. When a desired level of immunogenicity is obtained, the immunized animal can be bled and the serum isolated and stored, and/or the animal can be used to generate MAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified BPH-specific polypeptide (or any BPH composition, if used after tolerization to common antigens). The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986, pp 60–61), but mice are generally preferred, with the BALB/c mouse being most preferred as this is most routinely used and generally gives a higher percentage of stable fusions.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986, pp. 65–66; Campbell, 1984, pp 75–83, each incorporated herein by reference). For example, where the immunized animal is a mouse, one may use P3-X63/Ag8, X63-Ag8.653, NS1/ 1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line tha may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976); and those using polyethylene glycol (PEG), such as 37% (v/v) PEG, by Gefter et al. (1977). The use of electrically induced fusion methods is also appropriate (Goding, 1986, pp. 71–74).

Fusion procedures usually produce viable hybrids at low frequencies, about $1 \times 10^{-6}$ to $1 \times 10^{-8}$ However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

In certain aspects of the present invention, i.e., those in which a BPH-specific antigen has not been pre-selected for immunization, one will desire to select one or more hybridomas that produce an antibody that binds specifically to BPH cells or that binds to BPH cells to a greater extent than it binds to normal or malignant prostate cells. In any event, one will generally identify suitable antibody-producing hybridomas by differential screening using, e.g., an ELISA, RIA, IRMA, IIF, or similar immunoassay, using both BPH cells and other prostate cells. Once candidates have been identified, one may also test for the absence of reactivity to normal tissue cells. In this manner, hybridomas producing antibodies having an undesirably high level of cross-reactivity may be excluded.

The selected hybridomas would then be serially diluted and cloned into individual antibody-producing cell lines, which clones can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations.

Further purification of the MAbs may be accomplished by a variety of methods known to those of skill including, filtration, centrifugation, zone electrophoresis, precipitation by ammonium sulfate followed by dialysis against saline, and various chromatographic methods such as ion exchange, affinity or immunoaffinity chromatography, gel filtration and HPLC techniques (Goding, 1986, pp 104–126).

D. Antibody Conjugates

Antibody conjugate and immunotoxin technology is fairly well-advanced and known to those of skill in the art. First, concerning immunotoxins, these are agents that have an antibody component linked to another agent, particularly a cytotoxic or otherwise anticellular agent, having the ability to kill or suppress the growth or cell division of cells. The preparation of immunotoxins is, in general, well known in the art (see, e.g., U.S. Pat. No. 4,340,535, incorporated herein by reference). It is also known that while IgG based immunotoxins will typically exhibit better binding capability and slower blood clearance than their Fab' counterparts, Fab' fragment-based immunotoxins will generally exhibit better tissue penetrating capability as compared to IgG based immunotoxins.

Numerous types of disulfide-bond containing linkers are known which can successfully be employed to conjugate the toxin moiety with the binding agent, certain of which linkers will generally be preferred over other linkers, based on differing pharmacologic characteristics and capabilities. For example, linkers that contain a disulfide bond that is sterically "hindered" may be preferred, due to their greater stability in vivo, thus preventing release of the toxin moiety prior to binding at the site of action. Furthermore, while certain advantages in accordance with the invention will be realized through the use of any of a number of toxin moieties, the use of ricin A chain, and even more preferably deglycosylated A chain, will likely provide particular benefits.

A wide variety of cytotoxic agents are known that may be conjugated to anti-BPH cell antibodies. Examples include numerous useful plant-, fungus- and bacteria-derived toxins, which, by way of example, include various A chain toxins, particularly ricin A chain, ribosome inactivating proteins such as saporin or gelonin, α-sarcin, aspergillin, restrictocin, ribonucleases such as placental ribonuclease, angiogenin, diphtheria toxin, and pseudomonas exotoxin, to name just a few. The most preferred toxin moiety is toxin A chain which has been treated to modify or remove carbohydrate residues, so called deglycosylated A chain (dgA, which is available commercially, e.g., from Inland Laboratories, Austin, Tx).

However, it may be desirable from a pharmacologic standpoint to employ the smallest molecule possible that nevertheless provides an appropriate biological response. One may thus desire to employ smaller A chain peptides which will provide an adequate anti-cellular response. To this end, it has been discovered that ricin A chain may be "truncated" by the removal of 30 N-terminal amino acids by Nagarase (Sigma), and still retain an adequate toxin activity, and such truncated A chains may be employed.

Alternatively, one may find that the application of recombinant DNA technology to the toxin A chain moiety will provide additional benefits. In that the cloning and expression of biologically active ricin A chain has now been enabled, it is now possible to identify and prepare smaller or otherwise variant peptides which nevertheless exhibit an appropriate toxin activity. Moreover, the fact that ricin A chain has now been cloned allows the application of site-directed mutagenesis, through which one can readily prepare and screen for A chain derived peptides.

The cross-linking of a toxin to a BPH antibody may utilize a cross-linker that has a disulfide function. The reason for this is that the toxin moiety will be readily releasable from the binding agent once the agent has "delivered" the toxin to the targeted PBH cells. Each type of cross-linker, as well as how the cross-linking is performed, will tend to vary the pharmacodynamics of the resultant conjugate. Ultimately, one desires to have a conjugate that will remain intact under conditions found everywhere in the body except the intended site of action, at which point it is desirable that the conjugate have good "release" characteristics. Therefore, the particular cross-linking scheme, including in particular the particular cross-linking reagent used and the structures that are cross-linked, will be of some significance.

Cross-linking reagents are used to form molecular bridges that tie together functional groups of two different proteins (e.g., a toxin and an antibody). To link two different proteins in a step-wise manner, heterobifunctional cross-linkers can be used which eliminate the unwanted homopolymer formation. An exemplary heterobifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., dgA).

The spacer arm between these two reactive groups of any cross-linkers may have various length and chemical composition. A longer spacer arm allows a better flexibility of the conjugate components while some particular components in the bridge (e.g., benzene group) may lend extra stability to the reactive group or an increased resistance of the chemical link to the action of various aspects (e.g., disulfide bond resistant to reducing agents).

A preferred cross-linking reagent may be SMPT, which is a bifunctional cross-linker containing a disulfide bond that is "sterically hindered" by an adjacent benzene ring and methyl groups. It is believed that stearic hindrance of the disulfide bond serves a function of protecting the bond from attack by thiolate anions such as glutathione which can be present in tissues and blood, and thereby help in preventing decoupling of the conjugate prior to its delivery to the site of action by the binding agent. The SMPT cross-linking reagent, as with many other known cross-linking reagents, lends the ability to cross-link functional groups such as the SH of cysteine or primary amines (e.g., the epsilon amino group of lysine). Another possible type of cross-linker includes the heterobifunctional photoreactive phenylazides containing a clearable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

Although the "hindered" cross-linkers will generally be preferred in the practice of the invention, non-hindered linkers can be employed and advantages in accordance herewith nevertheless realized. Other useful cross-linkers, not considered to contain or generate a protected disulfide, include SATA, SPDP and 2-iminothiolane (Wawrzynczak & Thorpe, 1987). The use of such cross-linkers is well understood in the art.

Once conjugated, it will be important to purify the conjugate so as to remove contaminants such as unconjugated A chain or antibody. It is important to remove unconjugated A chain because of the possibility of increased toxicity. Moreover, it is important to remove unconjugated antibody to avoid the possibility of competition for the antigen between conjugated and unconjugated species. In any event, a number of purification techniques have been found to provide conjugates to a sufficient degree of purity to render them clinically useful.

In general, the most preferred technique will incorporate the use of Blue-Sepharose with a gel filtration or gel permeation step. Blue-Sepharose is a column matrix composed of Cibacron Blue 3GA and agarose, which has been found to be useful in the purification of immunoconjugates. The use of Blue-Sepharose combines the properties of ion exchange with A chain binding to provide good separation of conjugated from unconjugated binding. The Blue-Sepharose allows the elimination of the free (non conjugated) antibody from the conjugate preparation. To eliminate the free (unconjugated) toxin (e.g., dgA) a molecular exclusion chromatography step may be used using either conventional gel filtration procedure or high performance liquid chromatography.

After a sufficiently purified conjugate has been prepared, one will desire to prepare it into a pharmaceutical composition that may be administered parenterally. This is done by using for the last purification step a medium with a suitable pharmaceutical composition. Suitable pharmaceutical compositions in accordance with the invention will generally comprise from about 10 to about 100 mg of the desired conjugate admixed with an acceptable pharmaceutical diluent or excipient, such as a sterile aqueous solution, to give a final concentration of about 0.25 to about 2.5 mg/ml with respect to the conjugate. Such formulations will typically include buffers such as phosphate buffered saline (PBS), or additional additives such as pharmaceutical excipients, stabilizing agents such as BSA or HSA, or salts such as sodium chloride. For parenteral administration it is generally desirable to further render such compositions pharmaceutically acceptable by insuring their sterility, non-immunogenicity and non-pyrogenicity. Such techniques are generally well known in the art as exemplified by Remington's Pharmaceutical Sciences, 16th Ed. Mack Publishing Company, 1980, incorporated herein by reference. It should be appreciated that endotoxin contamination should be kept minimally at a safe level, for example, less that 0.5 ng/mg protein. Moreover, for human administration, preparations should meet sterility, pyrogenicity, general safety and purity standards as required by FDA Office of Biological Standards.

A preferred parenteral formulation of the immunotoxins in accordance with the present invention is 0.25 to 2.5 mg conjugate/ml in 0.15M NaCl aqueous solution at pH 7.5 to 9.0. The preparations may be stored frozen at $-10½$ C. to $-70½$ C. for at least 1 year.

Another group of antibody conjugates are those in which the antibody is linked to a chemotherapeutic agent. These include a wide variety of agents, such as antitumor drugs, cytokines, antimetabolites, alkylating agents, hormones, and the like, which may also be targeted to a BPH cell using an antibody conjugate. The advantages of these agents over their non-antibody conjugated counterparts is the added selectivity afforded by the antibody. One might mention, by way of example, agents such as steroids, cytosine arabinoside, methotrexate, aminopterin, anthracyclines, mitomycin C, vinca alkaloids, demecolcine, etoposide, mithramycin, and the like.

In analyzing the variety of chemotherapeutic and pharmacologic agents available for conjugating to an antibody, one may wish to particularly consider those that have been previously shown to be successfully conjugated to antibodies and to function pharmacologically (e.g., Vaickus et al., 1991). Exemplary antineoplastic agents that have been used include doxorubicin, daunomycin, methotrexate, vinblastine (Dillman et al., 1988; Pietersz et al., 1988). Moreover, the attachment of other agents such as neocarzinostatin (Kimura et al., 1983), macromycin, trenimon and $\alpha$-amanitin (Ghose, 1982) has also been described. The lists of suitable agents presented herein are, of course, merely exemplary in that the technology for attaching pharmaceutical agents to antibodies for specific delivery to tissues is well established.

Thus, it is generally believed to be possible to conjugate to antibodies any pharmacologic agent that has a primary or secondary amine group, hydrazide or hydrazine group, carboxyl alcohol, phosphate, or alkylating group available for binding or cross-linking to the amino acids or carbohydrate groups of the antibody. In the case of protein structures, this is most readily achieved by means of a cross linking agent, as described above for the immunotoxins. Attachment may also be achieved by means of an acid labile acyl hydrazone or cis aconityl linkage between the drug and the antibody, or by using a peptide spacer such as L-Leu-L-Ala-L-Leu-L-Ala, between the $\gamma$-carboxyl group of the drug and an amino acid of the antibody.

Yet another group of antibody conjugates that are contemplated to be particularly useful in connection with the present invention are those in which the BPH-restricted antibody is linked to a radioisotope. This group of targeted agents are particularly contemplated to be of use in therapeutic embodiments for use in treating patients with BPH. The technology for attaching ions to antibodies is well established. Many such methods involve the use of a metal chelate complex employing, for example, an organic chelating agent such a DTPA attached to the antibody (see, e.g., U.S. Pat. No. 4,472,509).

E. Pharmaceutical Preparations

This invention also contemplates the use of the BPH-specific antibodies, conjugates thereof, and particularly, antibodies conjugated to radioisotopes, in therapeutic embodiments. Such therapeutic compositions will generally comprise an effective amount of the BPH antibody, particularly, an anti-BP52 antibody conjugate, dissolved or dispersed in a pharmaceutically acceptable carrier or aqueous medium.

The phrases "pharmaceutically or pharmacologically acceptable" refers to molecular entities and compositions that do not produce an adverse, allergic or other untoward reaction when administered to a human. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The antibody conjugates for use in treating BPH will generally be prepared as formulations for parenteral administration, such as intravenous or intramuscular injection. However, other pharmaceutically acceptable forms are possible, including semi-permeable capsules and other biologically releasable forms.

An antibody, immunotoxin, antibody-drug or antibody radioisotope conjugate may be formulated for parenteral administration by preparing a composition suitable for injection, e.g., via the intravenous, intramuscular or subcutaneous routes. The preparation of an aqueous composition that contains an anti-BPH antibody or conjugate thereof as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

A BPH antibody or conjugate, such as a BP52-based composition, can be formulated for use in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active antibody-based compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus ny additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and even intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The physician responsible for administration will be able to determine the appropriate dose for the individual subject in light of the knowledge in the art in combination with the present disclosure.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

GENERATION OF BP52, A BPH-SPECIFIC MONOCLONAL ANTIBODY

1. Sources of Tissues and Biological Fluids

Samples of prostate tissue, serum, urine, seminal plasma and prostate fluid may be obtained from appropriate tissue banks, such as the tissue bank used in the present studies which is maintained by the Center for Urological Oncology at Eastern Virginia Medical School and located in the Department of Microbiology and Immunology. Tissues and samples for use in these studies include paraffin blocks of CaP (primary and metastatic) and BPH tissues; fresh frozen CaP and BPH specimens; serum samples from patients with various prostate diseases and other urological conditions, and normal age matched male donors; urine specimens from normal donors, patients with BPH, prostatitis and CaP; and prostate fluid and semen specimens from CaP and BPH patients.

Normal donors and patients are consented prior to collection of samples. Seminal plasma is collected by masturbation after at least 24 hrs of sexual abstinence. The samples are not allowed to liquefy by immediately diluting the sample with one-half volume of Tris-HCl, pH 8.0 containing 0.2M NaCl, KCl, $MgSO_4$, EDTA and the protease inhibitors phenylmethylsulfonylfluoride (PMSF), antipain and pepstatin. The samples are chilled to 4° C., vortex-mixed to ensure complete mixing, centrifuged at 25,000× g for 5 minutes, and the supernatant stored at −80° C. Prostate fluid is collected by rectal massage and processed for storage in the tissue bank as described for seminal plasma.

2. Preparation of Tolerogen

The tolerogen was prepared from surgically removed well-differentiated prostate carcinoma (CAP) tissue. The tissue was minced into small pieces and transferred to a 15 ml ounce tube containing 10 ml of 1 mM $NaHCO_3$ and 0.2 ml of protease inhibitor cocktail (3.4 mg antipain, 10.0 mg pepstatin, 0.372 g EDTA, dissolved in 20 ml $DDH_2O$) and 20 μl of 1 mM phenyl-methyl-sulfonyl-fluoride (PMSF). The tissue-buffer mixture was incubated on ice for 20 minutes and was then homogenized 5× (15 seconds on, 15 seconds off) with a Polytron tissue homogenizer. This homogenate was then dounced 10× with glass plungers (sizes A and B). The tissue homogenate was spun in 15 ml corex glass tubes for 5 minutes at 500× g at 4° C. The resulting supernatant was spun at 138,000× g for 2 hours at 4° C. The resulting pellet was resuspended in a small amount of 0.15M phosphate buffered saline (PBS). Protein determinations were made using the Pierce BCA protein assay method. The Protein concentration was adjusted to 1 mg/50 μl and the material was stored at −70° C. until needed.

3. Preparation of Immunogen

The immunogen used for this fusion was prepared from surgically removed benign prostate hyperplasia (BPH) tissue. The tissue preparation protocol was the same as described immediately above in section 2 for the tolerogen.

4. Immunotolerizing/Immunizing Protocol

Immunotolerance: Newborn BALB/c mice were tolerized every other day from the day of birth through day 10 by intraperitoneal (IP) injection of 50 μl of 1 mg/ml of the CaP tolerogen, prepared as described above.

Immunization: At 4 weeks of age the tolerized animals were immunized in the hind footpads (FP) with 0.05 mg and IP with 0.1 mg of the BPH immunogen, prepared as described above. The immunizing material was mixed 1:1 with Freund's complete adjuvant. The animals received four doses of the immunizing material on days 1, 5, 9, and 13.

5. Production and Screening of Hybridomas

Production: On day 14 following the immunization schedule described above, the mice were sacrificed by cervical dislocation and the splenic lymphocytes were harvested and disassociated into a single cell suspension by tissue mincing and progressively sieving through different gauge needles. Red blood cells were lysed with 0.84% ammonium chloride and the remaining lymphocytes (~1.3× $10^8$ cells) were washed and fused at a ratio of 2:1 with NS-1 myeloma cells in the presence of 50% PEG and plated in 96-well plates in Optimem I, 10%FBS and HAT selective medium (hypothantine, aminopterin, thymidine).

Screening: Supernatants from growing hybrids were screened initially by indirect radioimmunoassay (RIA) procedures in which membrane extracts (prepared as above) of CaP (tolerogen) and BPH (immunogen) were attached to microtiter plates, dried, and blocked with 2% bovine serum albumin (BSA). Twenty-five µl of hybridoma culture supernatant was added to each well, incubated for 1 hr at room temperature, washed, then incubated with 100,000 cpm/well of $^{125}$I-antimouse IgG (heavy and light chain) for 1 hour at room temperature. Following incubation, the wells were washed, dried cut, and counted in a gamma counter. Positive wells were considered to be those that showed counts per minute (cpms) at least three times that of the negative control antibody.

Positive hybridomas selected from the initial RIA screening were also screened immunohistochemically using the Vector ABC elite immunoperoxidase (IP) kit on both fixed and frozen tissue sections. Sections of formalin fixed and paraffin embedded tissues were deparaffinized in two changes of xylene and hydrated in a graded series of alcohols. Endogenous peroxidase was blocked by incubating hydrated sections or air-dried (30 minutes) frozen sections in methanol/hydrogen peroxide. From this point on, both types of tissue were handled the same.

Sections were blocked with 10% normal blocking serum (normal horse) for 10 minutes to prevent non specific binding. Primary antibody (hybridoma culture supernatant) was added and incubated with the tissue for 15 minutes, washed with PBS, and then biotinylated horse anti-mouse antibody was incubated with the tissue for 10 minutes. The tissue was again washed with PBS and incubated with the avidin-biotin complex (ABC) for an additional 10 minutes and washed again with PBS. The substrate and chromogen (1 ml of 0.2% DAB (diaminobenzedine HCl) in 3 ml of PBS plus 12 µl of hydrogen peroxide) were added and incubated for 5 minutes. Following a water wash the sections were counterstained with Mayer's hematoxylin and covermounted. The stained sections were examined by light microscopy and scored according to the number of cells staining (i.e., expressing the BP52 antigen) and staining intensity where 1+=weak; 2+=moderate; and 3+=strong intensity. The initial screen of BP52 by RIA yielded 16,400 cpms against the tolerogen and 150 cpms against the immunogen. By IP it showed 4+ staining against frozen BPH tissue and no reactivity against CaP. This hybrid was cloned by limiting dilution and plated at 0.1, 1, and 3 cells/well densities.

EXAMPLE II

PURIFICATION AND CHARACTERIZATION OF BP52

1. Production of Ascites Fluid

BALB/CBYJ, female mice, 10–11 weeks old, are primed by injecting 250 µl of Freund's incomplete adjuvant (IP) 7–10 days prior to injecting (IP) 2×$10^7$ BP52 hybridoma cells from the log phase of growth. Mice are observed for ascites formation (swelling of abdomen) which usually occurs 10–14 days post injection. Mice were then killed by cervical dislocation and the ascites was harvested from the abdominal cavity by aspiration. The ascites fluid was then spun for 10 min at 3000 rpm to remove red blood cells. Immunoglobulin production was measured by adding 5 µl of ascites diluted 1:10 with normal saline to the well of an appropriate immunoglobulin class radial immunodiffusion plate. The quantity of immunoglobulin produced was calculated by comparing the diameter of the immunodiffusion ring produced against a calibration/conversion chart. The ascites was stored frozen at −70° C. until ready for purification.

2. Isotyping of BP52

The BP52 isotype was determined by an ELISA (enzyme linked immunoabsorbent assay) capture assay. In this procedure a goat anti-mouse antibody was attached to a microtiter plate by incubating the antibody, diluted in PBS buffer, for 1 hour at 37° C. or at 4° C. overnight. The coating antibody was removed, the plate was washed and then 100 µl of BP52 antibody (culture supernatant) was added to each of 8 wells and incubated for 1 hour at room temperature. The BP52 antibody was removed, the plate was washed, and then 50 µl of each isotype specific (IgG1, IgG2a, IgG2b, IgG3, IgM, IgA, kappa and lambda light chain) goat anti-mouse antibody was added to each well and incubated for 1 hour at room temperature and again washed. Then 100 µl of appropriately diluted peroxidase labeled goat anti-mouse IgG (Fab specific) antibody was added to each well and incubated at room temperature for 30 minutes. The plate was again washed and then incubated with 100 µl of freshly prepared substrate (the substrate is prepared as follows: 5-Aminosalicylic acid is dissolved at 1 mg/ml in 0.02M sodium phosphate buffer, pH 6.8 and 0.1 ml of 1% hydrogen peroxide is added for every 10 ml of the 5-Aminosalicylic acid prepared) for 20–30 minutes. The development of a brown colored reaction product indicates a positive result.

The BP52 antibody was also isotyped using the Sigma isotyping stick method in which the above-type reactions are carried out on nitrocellulose membrane strips bound to an inert support. An isotyping strip was placed in an assay tube and 2–3 ml hybridoma supernatant was added and incubated for 30 minutes, followed by washing in PBS buffer containing Tween 20 and BSA. The strip was next incubated with a biotinylated antibody to mouse IgG's for 5 minutes and washed again. The strip was next incubated with ExtrAvidin Peroxidase for 5 minutes and again washed. The final incubation was incubated with freshly prepared substrate containing the chromogen (3-amino-9-ethylcarbazole in N,N-dimethyl formamide), substrate buffer (2.5M acetate buffer, pH 5.0), and substrate (2% $H_2O_2$) until the first sign of isotype was present. Positive controls were included on the stick.

BP52 was identified as having an IgM (kappa) isotype by both methods.

3. Purification of BP52 Antibody

Since BP52 is an IgM antibody it is preferably purified by a combination of cryoprecipitation and size exclusion chromatography as follows: First: ascites clarification was accomplished by passing crude ascites through glass wool and centrifuging the filtered ascites for 30 minutes at 13,000 rpm at 4° C. Second, cryoprecipitation: the clarified ascites was transferred to dialysis tubing (MW cutoff 12,000) and dialyzed against 10× the sample volume with distilled water for 24 hours at 4° C. The dialyzed material was centrifuged for 1 hour at 11,000–13,000 rpm at 4° C. The pellet recovered from the centrifugation was dissolved in <5.0 ml of PBS buffer.

Third: Size exclusion chromatography was performed on a Tosohaas SWG3000 column. The column was equilibrated with PBS buffer and SEC protein standards were run prior to loading the BP52 cryoprecipitated material. The dissolved, microfuged BP52 crude material was loaded onto the column and eluted with PBS buffer. The elution was monitored at $OD_{280}$, and the IgM was eluted in the first protein peak from the column. The purity of the antibody was determined by SDS polyacrylamide gel electrophoresis on a 10% reducing gel. On SDS-PAGE IgM heavy chain is ~70,000–80,000, while the light chain is 25,000. A myeloma isotype control was included as a positive control.

EXAMPLE III

SPECIFIC DETECTION OF BPH USING BP52

BP52 was purified from ascites fluid and used at 1:100 for immunostaining 5 u sections of frozen and formalin-fixed paraffin embedded tissues. Immunostaining was performed using the Vector ABC elite immunoperoxidase (IP) kit. Endogenous peroxidase was blocked by incubating the sections in methanol/hydrogen peroxide. The sections were then incubated with 10% normal horse serum for 10 minutes to block non-specific binding. Purified BP52 antibody (1:100) was added and the sections incubated for 15 minutes, the sections washed with PBS, and then incubated with biotinylated horse anti-mouse antibody for 10 minutes. The sections washed with PBS and incubated with the avidin-biotin complex (ABC) for an additional 10 minutes, and the sections washed again with PBS. The substrate and chromogen (1 ml of 0.2% DAB (diaminobenzedine HCL) in 3 ml of PBS plus 12ul of hydrogen peroxide) were added and incubated for 15 minutes. Following a water wash the sections 5 were counterstained with Mayer's hematoxylin and covermounted. The stained tissue section were evaluated with the aid of a light microscope and the sections scored on the basis of the number or percent of the cells expressing the BP52 antigen (i.e., brown staining reaction) and intensity of the staining reaction. To determine the percent of cells staining with BP52, 10 different fields of 100 cells in each field were evaluated. The percent of stained cells was then determined by dividing the total number of stained cells by 10. Staining intensity was determined using the following scale: 1+=weak (pale); 2+=moderate; and 3+=strong (dark).

The BP52 marker was detected in 75% (9/12) and 100% (15/15) BPH frozen and fixed specimens, respectively (Table 1). Staining of benign ductal epithelial cells in these specimens ranged from 20% to 90% (mean 72%) (Tables 1 and 2). Because BP52 reactivity was observed in both formalin-fixed, paraffin-embedded specimens and frozen tissues, the antigen recognized by BP52 does not appear to be affected by fixation.

Similar results were obtained using a radioimmunoassay to detect the BP52 antigen in tissue extracts. For the RIA procedure, 1–5 ug of tissue extract or purified antigen was added to wells of microtiter plates, dried, and blocked with 2% bovine serum albumin. Five to 25 µl of purified BP52 or irrelevant control antibody (IgM isotype) was added to each well, incubated for 1 hour at room temperature, washed, then incubated with 100,000 cpm/well of 125I-antimouse IgG for 1 hour at room temperature. The wells were washed, dried and cut out from the plate and counted in a gamma counter. Positive wells were considered to be those that had at least 3 times the counts per minute (cpm) of the negative control antibody.

Five or six BPH extracts, 1 of 6 CaP extracts, and 0 of 1 pooled normal prostate tissue extract were bound by the BP52 MAb (Table 3). Weak reactivity was observed in 1/4 normal breast, 0/5 normal colon, 0/3 normal urinary bladder, and 0/3 normal urethra. The BP52 Mab also did not react to purified preparations of prostatic acid phosphatase (PAP) and prostate specific antigen (PSA), two well studied prostate tumor-associated markers (Table 3).

Initial studies with MAb BP52 did not detect the BP52 antigen in body fluids (i.e, serum, seminal plasma) by immunoblotting or by RIA. This might suggest that the antigen is neither secreted nor shed, or that the antigenic epitope cannot be effectively bound by this IgM antibody in the assay formats employed. Indeed, antibodies of the IgM isotype are known to be quite unstable (Matthew & Sandrock, 1987).

Using the immunohistochemical methods, about 3% staining of the ductal epithelial cells in normal prostate specimens was observed; and about 10% of the tumor cells were stained in CaP tissues (Tables 2 and 4). Most all the staining in CaP tissues was confined to the well- to moderately-differentiated tumor areas. BP52 expression was not observed in non-prostate normal tissues, with the exception of scattered staining of kidney tubules, or in other malignant tissues (Tables 5–8).

MAb BP52 is proposed to be a useful agent for the immunohistopathological identification of BPH in tissue sections, used either alone or in combination with a marker specific for CaP, such as the MAb termed PD41. The reactivity of MAbs BP52 and PD41 on BPH and CaP tissue sections was compared. BP52 stained the benign luminal epithelial cells but not the malignant tumor cells whereas PD41 stained the malignant cells in both the primary and metastatic prostate carcinomas but not BPH. Thus, the BP52 MAb recognizes a unique BPH biomarker and is capable of distinguishing BPH from CaP. These results illustrate the use of BP52, and the combined use of BP52 and PD41, for differentiating benign from malignant prostate tumor cells.

TABLE 1

SUMMARY OF THE IMMUNOPEROXIDASE REACTIVITY OF MAB BP52 TO FIXED AND FROZEN PROSTATE TISSUE SPECIMENS

| TISSUE | FROZEN | | | FIXED | | |
|---|---|---|---|---|---|---|
| | No. Pos./No. Tested | (%) | Mean % Cells Pos. | No. Pos./No. Tested | (%) | Mean % Cells Pos. |
| NORMAL | 4/7 | (57) | 2.5 | 12/15 | (80) | 3.3 |
| BENIGN PROSTATIC HYPERPLASIA | 9/12 | (75) | 76.0 | 15/15 | (100) | 68.0 |
| PRIMARY CARCINOMA | 4/14 | (29) | 6.2 | 8/21 | (38) | 10.3 |

TABLE 2

IMMUNOPEROXIDASE STAINING OF PROSTATE TISSUES WITH MONOCLONAL ANTIBODY BP52
(Formalin-fixed paraffin-embedded tissues)
(1:100 BP52 purified from ascites)

| Benign Prostate Hyperplasia | Percent | Intensity |
|---|---|---|
| Ca2374-1 | 80 | 1–2+ |
| Ca2375-3 | 80 | 1–2+ |
| Ca2376-1 | 80 | 1–3+ |
| Ca2378-1 | 30 | 1+ |
| Ca2379-4 | 70 | 1–2+ |
| Ca2380-1 | 70 | 1–2+ |
| Ca2400-1 | 70 | 1–2+ |
| Ca2372-2 | 60 | 1–3+ |
| Ca2381-1 | 80 | 1–3+ |
| Ca2388-3 | 80 | 1–3+ |
| Ca2390-1 | 80 | 1–3+ |
| Ca2391-1 | 65 | 1–3+ |
| Ca2397-1 | 30 | 1–2+ |
| Ca2399-3 | 70 | 1–3+ |
| Ca2400-1 | 70 | 1–2+ |
| (15/15 = 100%; mean cell staining = 68%) | | |

Normal Prostate

| | | |
|---|---|---|
| Ca2068C | <5 | 1–2+ |
| Ca2074A | <1 | 1+ |
| Ca2075C | <1 | 1+ |
| Ca2081B | <5 | 1–2+ |
| Ca2091B | <5 | 1–2+ |
| Ca2123C | <1 | 1–2+ |
| Ca2206B | <5 | 1–2+ |
| Ca2291B | <5 | 1–2 |
| Ca2077B | 0 | 0 |
| Ca2079B | <1 | 1+ |

| Benign Prostate Hyperplasia | Percent | Intensity |
|---|---|---|
| Ca2082C | 0 | 0 |
| Ca2114C | <5 | 1+ |
| Ca2118A | 0 | 0 |
| Ca2213A | <5 | 1+ |

TABLE 2-continued

IMMUNOPEROXIDASE STAINING OF PROSTATE TISSUES WITH MONOCLONAL ANTIBODY BP52
(Formalin-fixed paraffin-embedded tissues)
(1:100 BP52 purified from ascites)

| | | | |
|---|---|---|---|
| Ca2292B | | 10 | 1+ |
| (12/15 = 80%; mean cell staining = 3.3%) | | | |

Prostate Carcinoma

| | | | |
|---|---|---|---|
| Ca1221A | W | 0 | 0 |
| Ca2670 | W | 60 | 1+ |
| Ca2455 | W | <1 | 1+ |
| Ca2531 | W | 0 | 0 |
| Ca2537 | W–M | 30 | 1+ |
| Ca2468A | W–M | 20 | 1+ |
| Ca2552 | W–M | 0 | 0 |
| Ca2575 | W–M | 15 | 1+ |
| Ca2627 | W–M | 0 | 0 |
| Ca2635A | W–M | 0 | 0 |
| Ca2439 | M | 75 | 1+ |
| Ca2578 | M | 10 | 1+ |
| Ca2512 | M–P | 0 | 0 |
| Ca2543 | M–P | 0 | 0 |
| Ca2652A | M–P | 0 | 0 |
| Ca2536 | P | 0 | 0 |
| Ca1220B | P | <5 | 1+ |
| Ca2561 | P | 0 | 0 |
| Ca2582B | P | 0 | 0 |
| Ca2587A | P | 0 | 0 |
| Ca2641 | P | 0 | 0 |
| (8/21 = 38%; mean cell staining = 10.3%) | | | |

TABLE 3

REACTIVITY OF MAB BP52 TP PROSTATE ANTIGENS BY RADIOIMMUNOASSAY

| | CPM | | BINDING | NO. POS/TESTED |
|---|---|---|---|---|
| TARGET ANTIGEN | BP52 | CONTROL MAB | RATIO | (>3.0) |
| BPH | | | | |
| CA1242 | 2170 | 460 | 4.7 | |
| P-54 | 1432 | 511 | 2.8 | |
| CA1775 | 1447 | 318 | 4.6 | 5/6 |
| CA1820 | 1511 | 209 | 7.2 | |
| CA1484 | 849 | 166 | 5.1 | |
| P-67 | 764 | 229 | 3.9 | |
| CARCINOMA | | | | |
| WD P-57 | 635 | 406 | 1.6 | |
| MD P-34 | 864 | 204 | 4.2 | |
| MD CA1286 | 175 | 205 | 0.9 | 1/6 |
| MD/PD CA181 | 366 | 239 | 1.5 | |
| PD CA1788 | 118 | 130 | 0.9 | |
| PD P-21 | 623 | 295 | 2.1 | |
| NORMAL PROSTATE POOL | 449 | 197 | 2.3 | 0/1 |
| PAP ANTIGEN | 357 | 238 | 1.5 | 0/1 |
| PSA ANTIGEN | 186 | 82 | 2.3 | 0/1 |

BINDING RATIO: CPM OF BP52 DIVIDED BY CPM OF CONTROL ANTIBODY.

TABLE 4

MoAB BP52 REACTIVITY VERSUS PATHOLOGICAL GRADE OF PROSTATE CARCINOMA

| PATHOLOGICAL GRADE GLEASON SUM (G) | NO. POS./ NO. TESTED | (%) | MEAN % DUCTS/CELLS POS. |
|---|---|---|---|
| Well Differentiated G 1–4 | 2/7 | (29) | <1 |
| Moderately Differentiated G 5–7 | 9/23 | (39) | 17 |
| Poorly Differentiated G 8–10 | 0/11 | (0) | 0 |

TABLE 5

IMMUNOPEROXIDASE STAINING OF NON-PROSTATE NORMAL TISSUES
(Formalin-fixed paraffin embedded tissues)
(1:100 BP52 purified from ascites)

| Tissue | Code # | Percent | Intensity |
|---|---|---|---|
| Breast | Ca1057A | 0 | |
| | NGH-2 | 0 | |
| | NGH-3 | 0 | |
| Adrenal | Ca2248 | 0 | |
| | Ca2258 | 0 | |
| | Ca2274 | 0 | |
| Colon | Ca1026B | 0 | |
| | Ca2096A | 0 | |
| | Ca2277B | 0 | |
| Pancreas | Ca1025A | 0 | |
| | Ca1026A | 0 | |
| | Ca2333 | 0 | |
| Spleen | Ca1138B | 0 | |
| | Ca2257A | 0 | |
| | Ca2274A | 0 | |
| Kidney | Ca1247B | Scat. (tubules) | 1–3+ |
| | Ca2239 | Scat. (tubules) | 1–3+ |
| | Ca2240 | Scat. (tubules) | 1–3+ |
| Lung | Ca1138B | 0 | |
| | Ca1247 | 0 | |
| | Ca1509A | 0 | |
| Liver | Ca1013A | 0 | |
| | Ca1025 | 0 | |
| | Ca1247A | 0 | |
| Testicle | Ca1060A | 0 | |
| | Ca1067B | 0 | |
| | Ca2214B | 0 | |
| | Ca2271 | 0 | |
| | Ca2323B | 0 | |
| Ovary | Ca1026A | 0 | |
| | Ca1030 | 0 | |
| | Ca1179B | 0 | |
| | Ca1196B | 0 | |

TABLE 6

IMMUNOPEROXIDASE REACTIVITY OF MONOCLONAL ANTIBODY BP52 ON FROZEN NORMAL TISSUE SPECIMENS

| TISSUE | NUMBER POSITIVE/TESTED | TISSUE | NUMBER POSITIVE/TESTED |
|---|---|---|---|
| ADRENAL | 0/2 | LYMPH NODE[B] | 4/5 |
| BLADDER | 0/4 | MUSCLE | 0/3 |
| BRAIN | 0/4 | OVARY | 0/3 |
| BREAST | 1/4[A] | PANCREAS | 0/5 |
| COLON | 0/3 | NERVE | 0/4 |
| ESOPHAGUS | 0/3 | SKIN | 0/4 |
| HEART | 0/3 | SMALL BOWEL | 0/1 |
| KIDNEY | 0/1 | SPLEEN | 0/4 |

TABLE 6-continued

IMMUNOPEROXIDASE REACTIVITY OF MONOCLONAL ANTIBODY
BP52 ON FROZEN NORMAL TISSUE SPECIMENS

| TISSUE | NUMBER POSITIVE/TESTED | TISSUE | NUMBER POSITIVE/TESTED |
|---|---|---|---|
| LIVER | 0/2 | TESTICLE | 0/1 |
| LUNG | 0/2 | URETER | 0/3 |
|  |  | UTERUS[c] | 1/4 |

[A]LACTATING.
[B]MEMBRANE STAINING OF LYMPHOCYTES WITH LARGE GRANULES.
[C]SCATTERED STAINING IN TUBULES.

TABLE 7

IMMUNOPEROXIDASE STAINING OF NORMAL
LYMPH NODES WITH MAb BP52
(Formalin-fixed paraffin embedded tissues)

| Code # | BP52 dilution 1:100 | 1:40 |
|---|---|---|
| Ca1015A | 0 | NT |
| Ca1025A | 0 | 0 |
| Ca1030A | 0 | <1 |
| Ca1054A | NT | 0 |
| Ca1057A | 0 | 0 |
| Ca1058B | 0 | 0 |
| Ca1058B | NT | 0 |
| Ca1064A | 0 | NT |
| Ca1148B | 0 | <1 |
| Ca1154A | 0 | NT |

TABLE 8

IMMUNOPEROXIDASE STAINING OF NON-PROSTATE
FORMALIN-FIXED PARAFFIN EMBEDDED CANCERS
(1:100 BP52 purified from ascites)

| Tissue | Code # | Percent | Intensity |
|---|---|---|---|
| Breast | Ca1304B | 0 | 0 |
|  | Ca1969C | 0 | 0 |
|  | Ca2014A | 0 | 0 |
| Colon | Ca1327A | 0 | 0 |
|  | Ca1350A | 0 | 0 |
|  | Ca1677 | 0 | 0 |
| Pancreas | VAS-1637-83 | 0 | 0 |
|  | VAS-1466-83 | 0 | 0 |
|  | NGH 80-2505C | 0 | 0 |
| Lung | CA1349 | 0 | 0 |
|  | VAS-37-85B | 0 | 0 |
|  | VAS-2521-83C | 0 | 0 |
| Liver | Ca1037A | 0 | 0 |
|  | Ca1166A | 0 | 0 |
| Kidney | Ca1016 | 0 | 0 |
|  | Ca1389A | 0 | 0 |
|  | Ca2289 | 0 | 0 |
|  | Ca1147A | 0 | 0 |
|  | Ca2084B | 0 | 0 |
|  | Ca2568 | 0 | 0 |
| Bladder | Ca1111B | 0 | 0 |
|  | Ca1138A | 0 | 0 |
|  | Ca1753A | 0 | 0 |
| Ovary | 89-4347A2 | 0 | 0 |
|  | 90-1657C2 | 0 | 0 |
|  | 89-1999D | 0 | 0 |
| Lymphoma | Ca1138B | 0 | 0 |

BP52 reactivity with prostate needle biopsies was also tested. It was found that the reactivity could not be evaluated based on number of cells positive because often the staining was confined to luminal secretions. Therefore, reactivity was based on the number of ducts or nests of cells expressing the BP52 antigen. Scoring in this manner essentially confirmed the original observations that BPH ducts expressing BP52 were clearly delineated from carcinoma in 22/29 specimens or 76% of the CaP specimens. The results of the core biopsy study is shown in Table 9.

TABLE 9

| PARTHOLOGICAL DIAGNOSIS | NO. TESTED | NO. POSITIVE | NO. WITH BENIGN DUCTS | PERCENT BPH CORRECTLY IDENTIFIED |
|---|---|---|---|---|
| ATYPIA | 13 | 7 | 7 | 100 |
| PROSTATITIS | 13 | 9 | 13 | 69 |
| HYPERPLASIA | 12 | 6 | 6 | 100 |
| BPH | 17 | 14 | 17 | 82 |
| PIN | 7 | 5 | 5[a] | 100 |
| CARCINOMA | 29 | 12 | 11 | 92 |

[a]BP52 reactivity also observed in the PIN lesions.
NP = none present.

EXAMPLE IV

ANTIBODIES THAT BIND TO THE SAME EPITOPE AS BP52

A series of immunoradiometric assay studies are used to determine BP52 MAID cross reactivity with other antigens, as described below:

1. Reciprocal Blocking Studies

BPH tissue extracts (prepared as described for tolerogen and. immunogen preparation) or other appropriate antigen for each test antibody evaluated are attached to microtiter plates for use as target antigens in a solid phase RIA. A range of concentrations (0–100 ug/ml) of BP52 (blocking antibody) are incubated with the target antigen(s) for 2 hours at room temperature, washed, and then incubated with a non-saturating amount of $^{125}$I-labeled test antibody (tracer antibody) for an additional 1 hour at room temperature. The wells are again washed, dried, and the radioactivity remaining in the wells is determined in a gamma counter.

If BP52 cross reacts with any of the test antibodies it is able to block the binding of the $^{125}$I-labeled non-BP52 tracer antibodies. In the reciprocal studies, the test antibodies are used as both blocking and tracer antibodies; blocking would occur in the homologous systems.

2. Competitive Blocking Studies

BP52 antigen-containing material, bound to MAb BP52 attached to a microtiter plate ("catcher antibody") is incubated with 100 ug/ml of unlabeled competing antibody (other anti-prostate, blood group related antibodies, etc.) for 2 hours at room temperature. Non-saturating amounts of $^{125}$I-labeled BP52 ("tracer antibody") are added and incubated for 1 hour at room temperature, then the wells are washed and again bound radioactivity determined in a gamma counter. If the competing antibodies blocked labeled MAb BP52 binding to the target antigens, this indicates some shared antigenic determinants or "cross-reacting" epitopes.

3. Direct Binding Assays

Direct binding of MAb BP52 to cell lines (both normal and tumor) of different tissue origin as well as membrane extracts from both normal and tumor tissues is assessable by solid-phase RIA. Values of more than 3 times the negative control (isotype matched) antibody would be indicative of MAb BP52 reactivity to other than BPH or prostate antigens.

EXAMPLE V

IDENTIFYING THE TARGET ANTIGEN REACTIVE WITH BP52

Isolation and purification of the reactive antigen from tissue extracts or body fluids is achieved by BP52 affinity chromatography (Dermer et al., 1982) or by a combination of molecular exclusion chromatography and BP52 affinity chromatography. Purity is assessable, for example, by the identification of a single molecular species by one-dimensional acrylamide gel electrophoresis.

The biochemical nature of the purified BP52 antigen is determined by subjecting the purified antigen to physical (i.e., heat), chemical (i.e., acids, alkali, organic solvents) and enzymatic (i.e., proteases, carbohydrases, lipases) treatments. Such treatments will reveal if the BP52 antigen contains carbohydrate, protein or lipid residues. The amino acid sequence of the purified BP52 antigen (or its core protein) is determinable using an automated peptide sequencer. The sequence may be compared with know protein sequences to determine if the BP52 protein has any sequence homology with known proteins. Based on the amino acid sequence data, synthetic oligonucleotides are prepared and used to screen a BPH-cDNA library to identify the cDNA encoding for the BP52 antigen. An alternate, but less sensitive, approach to identify the BP52 gene is to screen the BPH-cDNA library with purified BP52 MAID. Success with the latter approach depends on the affinity of the BP52 MAb; i.e., high affinity antibodies are required to successfully bind to the nucleoprotein expressed by the bacterial clone. Once the BP52 gene is isolated it can be inserted into an expression vector, and the vector inserted into a mammalian or bacterial cell to produce recombinant BP52.

From these studies synthetic peptides can be prepared and used to map the nature and site of the antigenic epitope using competitive binding immunoassays. The smallest peptide to maximally block the binding of native BP52 MAb would indicated the nature of the antigenic epitope. This peptide, purified native BP52 and recombinant BP52 antigen can all be used to produce second generation antibodies of the IgG isotype by the lymphocyte hybridoma technique (Beckett et al., 1991). Such antibodies could be employed to enhance the development of an immunoassay for measuring BP52 antigen, including BP52 antigen levels in body fluids.

The synthetic BP52 peptides and the BP52 gene (cDNA) could also be employed to develop specific BPH vaccines. A BP52-virus recombinant vaccine could be prepared by inserting the complete coding sequence for BP52 into a vaccinia virus genome (Kantor et al., 1992). Another approach is to prepare a polynucleotide vaccine by constructing a DNA plasmid encoding the full length cDNA for BP52 containing the cytomegalovirus early promoter/enhancer to drive expression of the BP52 gene (Conry et al., 1994).

EXAMPLE VI

MOLECULAR BIOLOGICAL METHODS TO IDENTIFY BPH-SPECIFIC PROTEINS

Further approaches to identify differentially expressed genes from BPH and CaP tissues are those employing molecular biological methods, for example, subtractive hybridization and differential display (Tanaka et al., 1992). These methods involve constructing cDNA libraries; isolating BPH- and CaP-specific cDNA clones by subtractive hybridization; and identifying differentially expressed mRNAs by reverse transcription and polymerase chain reaction. Using the molecular biological approach, BPH specific cDNAs can be isolated and directly cloned, allowing large amounts of protein to be easily generated for antibody generation and molecular characterization.

There are several methods that could be used to isolate unique BPH cDNAs. Subtracted probes can be used to screen BPH cDNA or subtracted libraries. The disadvantage with this method is that large amounts of poly A+ mRNA are needed. In addition, low copy messages will not be labeled to a high specific activity which creates problems for detection of rare or low abundant clones. Because the source of BPH and prostate carcinoma is from surgical samples, large amounts of message are not easily obtained and this limits the usefulness of this technique. For this reason, the inventor generated subtracted libraries from existing cDNA libraries. The subtracted libraries are screened by differential hybridization using cDNA probes generated from the existing libraries. The advantage with this technique is that only small amounts of messenger RNA are required to make the initial library.

1. cDNA Libraries

Normal prostate, BPH and CaP cDNA libraries were constructed using fresh histopathologically and immunologically confirmed tissues. Normal prostate tissue was procured from the living donor program thorough LifeNet Transplant services. BPH and CaP tissues were obtained from patients undergoing surgical treatment (Table 10), and from the LNCaP prostate carcinoma cell line. mRNA was isolated from fresh tissue using the Fast Track isolation kit (Invitrogen), double-stranded cDNA was synthesized using ZAP-cDNA synthesis kit (Stratagene), cloned into an alpha-ZAP XR expression vector, and the libraries expressed in *E. coli* strain Sure.

To test the integrity of the construct, the cDNA libraries were screened with affinity purified MAb against PSA, and polyclonal antibodies to PAP, PSA and PSP, using the Promega immunoscreening system. Positive plaques expressing the three proteins were identified in all three cDNA libraries, and a human prostate cDNA library purchased from Clontech (Palo Alto). The positive clones were carried through two or three rounds of screening until all phages produced positive signals. Recombinant phage cDNA inserts were subcloned into the EcoRI site of the plasmid vector, pUC18, amplified in *E. coli*, and the nucleotide sequences determined. Computer analysis of the nucleotide sequences and the deduced amino acid sequence confirmed that cDNAs were isolated for each of the 3 biomarkers. These results indicate that all three cDNA libraries were properly constructed.

For ease of manipulation and evaluation, the cDNAs were rescued into pBluescript, and the double-stranded plasmid cDNA inserts were isolated, digested with XhoI and EcoRI, and run on an agarose gel. The characteristics of the libraries are shown in Table 11. The size of the cDNA inserts for BPH and CaP ranged from 500 bp to 3kb. Normal prostate cDNA inserts are in the process of being rescued. These cDNA libraries are for use in the search for cDNAs encoding unique prostate disease biomarkers.

TABLE 10

PATHOLOGY AND IMMUNOPATHOLOGY PROFILES OF NPr, BPH, AND CaP TISSUES USED FOR cDNA LIBRARY CONSTRUCTION.

| Tissue | Gleason Score | MAb Reactivity (% positive cells) | | | |
|---|---|---|---|---|---|
| | | PSA | PD41 | TURP27 | 7E11 |
| Normal | NA | Nt | Nt | Nt | Nt |
| BPH | NA | 100 | 0 | 98 | 55 |
| CaP* | 5 | 80 | 0 | 10 | 40 |

*Poorly differentiated adenocarcinoma
NA = Not applicable;
Nt = not tested

TABLE 11

CHARACTERISTICS OF THE PROSTATE TISSUE cDNA LIBRARIES

| | Normal | BPH | CaP |
|---|---|---|---|
| mRNA (starting material) | 5 µg | 5 µg | 5 µg |
| Expression vector | λZAP | λZAP | λZAP |
| Primary library size | 2.5 × 10⁵ pfu | 8.8 × 10⁵ pfu | 2.0 × 10⁶ pfu |
| Titer after | 5.0 × 10⁹ | 3.8 × 10¹⁰ | 8.5 × 10⁹ |

TABLE 11-continued

CHARACTERISTICS OF THE PROSTATE TISSUE cDNA LIBRARIES

| | Normal | BPH | CaP |
|---|---|---|---|
| amplification | pfu/ml | pfu/ml | pfu/ml |
| PSA Mab screening | positive | positive | positive |

2. Subtractive Hybridization

The second phase of this study was the application of subtractive hybridization to identify unique BPH and CaP cDNAs, which approach is illustrated in FIG. 1. The plasmid BPH cDNA library (target) was used to generate single-stranded circular DNA using helper phage R408. The double-stranded plasmid DNA from the CaP library was used to synthesize biotinylated run-off transcripts. Single-stranded cDNAs from the target library (BPH) were annealed to the biotinylated RNA from the driver (CAP) library. After hybridization, the mixture was incubated with vectrex-avidin to separate the unbound fraction which was enriched with BPH specific single-stranded cDNAs. This unbound fraction was used to transform XL1-Blue cells resulting in a BPH-specific subtracted cDNA library. A CaP-specific subtracted cDNA library was prepared using the same protocol.

Seventeen BPH-specific and 210 CaP-specific clones have been isolated to date. The restriction enzyme digestion (XhoI and EcoRI) studies show that both subtracted libraries contain varied sizes of inserts. Northern blot analysis of total RNA isolated from various normal prostate, BPH, and CaP tissues is used to confirm that the BPH-specific subtracted cDNA clones react only with BPH and not also to normal and CaP.

Figure 2:
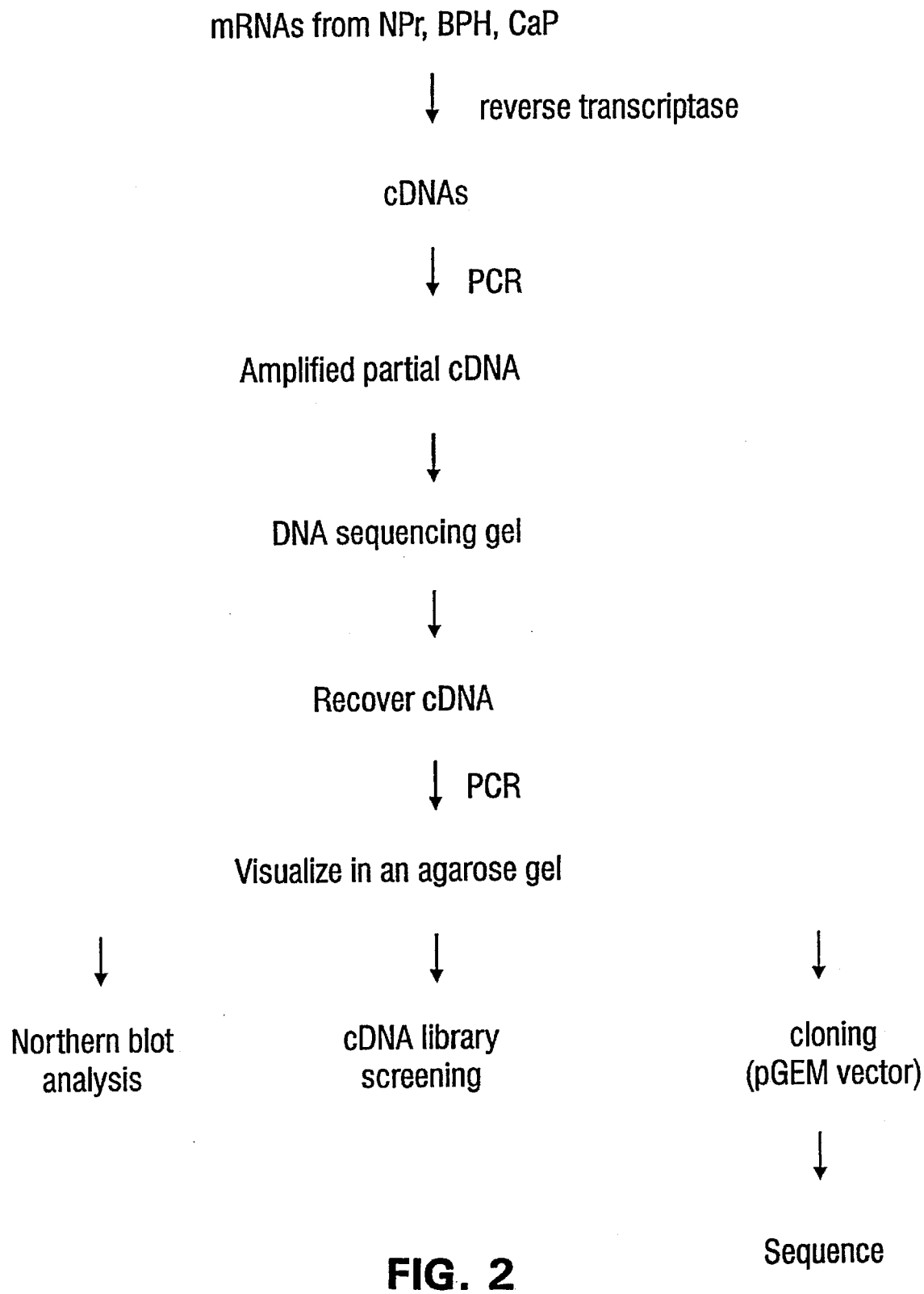
FIG. 2 Schematic outline of differential display.

The general scheme for identifying differentially expressed mRNAs is shown in FIG. 2. Partial cDNA sequences were obtained by amplifying subsets of mRNA using reverse transcription, polymerase chain reaction (PCR), and 3' and 5' synthetic oligo primers. The short sequences were then displayed on a sequencing gel. When normal prostate, BPH and CaP were compared, most bands were the same, but a few bands, were observed only in BPH, whereas others were found only in CaP. Some bands appeared in both BPH and CaP but were not evident in normal prostate. cDNA of these mRNA species are recoverable from DNA sequencing gels and may then be reamplified by PCR. The reamplified product is used in Northern blot analysis to confirm the differential expression, for screening cDNA libraries to isolate full length cDNA, and for cloning into pGEM vector for sequencing. These preliminary results suggest that specific genes exist for both BPH and CaP do exist.

To identify the BPH transcripts that are not found in normal or CaP libraries, the normal and CaP libraries may be pooled prior to subtraction. This pooled library, containing normal and CaP specific transcripts (minus library), is then subtracted from the BPH library (plus library). The advantage with this approach is that only one subtraction needs to be performed. This reduces the amount of screening necessary in the following steps.

BPH-specific clones will be subcloned into plasmid vectors for DNA sequence analysis. They will also be cloned into a bacterial expression vector such as pTrc-His (invitrogene) in order to generate large amounts of purified protein (Hughes et al., 1992). This expression system fuses 5 histidine residues to the amino terminus of the protein of interest. The histidine residues allow the newly synthesized protein to be purified easily by passage over a probond resin (invitrogene) which specifically binds to the histidine residues. The purified protein can then be eluted and used to generate polyclonal or monoclonal antibodies.

If a large number of independent BPH specific isolates are identified, each will be expressed in pools. These pools of recombinant proteins will be used to generate polyclonal antibodies. Polyclonal antibodies generated from these recombinant protein pools will then be assayed for their ability to detect BPH specific proteins in seminal plasma. Two-dimensional gels of normal, BPH, prostatitis, and CaP seminal plasma will be immunoblotted with polyclonal antibodies produced against the different pools of recombinant proteins. The polyclonal antisera that identifies a novel BPH protein will be absorbed with each of the individual recombinant proteins in the pool. Western blots of BPH seminal plasma will be repeated using the absorbed antisera to identify the clone producing the novel protein. Large amounts of the specific recombinant protein will then be purified and used to produce MAbs.

EXAMPLE VII

2-D GEL ELECTROPHORESIS TO IDENTIFY BPH-SPECIFIC PROTEINS

Another means for identifying specific biomarkers with the potential to differentiate BPH from CaP is to use two dimensional (2-D) gel electrophoresis to identify unique proteins.

For this approach, a tissue extract or seminal plasma, is first separated by isoelectric focusing followed by a second separation in an SDS gradient acrylamide gel. By comparing each 2-D protein pattern, spots unique to a particular tissue type can be identified. Previous difficulties in identifying subtle differences in 2-D profiles can now be virtually eliminated using computer-assisted imaging systems (Lee et al., 1989; Lee et al., 1988). Such systems can match profiles, subtract the common protein spots and produce a new profile representative of the distinct spots. Both qualitative and quantitative differences can be determined.

Using these methods, unique spots can be identified, then removed from the gel and used, e.g., as an immunogen to generate specific MAbs or analyzed further, e.g., by sequencing. More specifically, preparative 2-D gels will be prepared and the gel containing the protein spots either (Berry et al., 1984) cut out of the gel by overlaying the gel with a transparent plastic computer generated template, and the proteins electroeluted from the gel with a Amicon Micro-Electroeluter; or (Vital and Health Statistics, 1986) the proteins transferred to a PVDF-membrane, the membrane containing the bound protein cut out and used to determine the amino acid sequence (e.g., using automated NH3-terminal Edman degradation). The sequencing may be employed to determine which proteins to use as immunogens, for example, proteins having less than 20% homology with known proteins (GENBANK and EMBL libraries) may be employed to design synthetic peptides for immunization (peptides may be prepared using an automated peptide synthesizer and purified using reverse phase HPLC).

The basic 2-D separation techniques are described by Willard et al. (1979), Lee et al. (1986), Edwards et al. (1981), Johnson et al. (1985), Tollaksen et al. (1984) and Anderson et al. (1985). Optimal conditions for computer imaging are determined using carbamylated creating kinase. Suitable molecular weight markers for use as internal standards and profile accurate alignment are amyloglucosidase, ovalbumin, carbonic anhydrase and myoglobin (Sigma).

The inventor has optimized the first- and second-dimension parameters to allow maximum separation of proteins in BPH and CaP tissue extracts and seminal plasma. The optimal isoelectric point range, ampholite mixture and concentration, buffer conditions, running time, percent gel gradient, length of the first and second separations, protein concentration, and protein staining conditions have been determined. It was found that an isoelectric focusing range from pI 4.0 to pI 8.5 stretched over 18 cm gel width for the first dimension, and the proteins separated in a 4–20% gradient 20–24 cm gel for the second dimension, optimally separate the protein species.

One particular 2-D protein profile comparison between BPH and CaP has been generated. Seminal plasma (200 µg) was first separated in a 3 % isoelectric focusing gel (pH 4.5–7.5), and the focused proteins separated in the second direction in a 10–20% gel gradient. The narrow pH in the first direction and the length of the second direction (20 cm) allowed for maximum separation of the protein species. Over 100 protein stained (silver stain) spots are observed on the wet 2-D gels. Although comparison by manual analysis of the BPH and CaP gels shows that the protein patterns are very similar, there are obvious differences (both qualitative and quantitative) in the two profiles, especially the region below 30,000 daltons.

Several hundred proteins spots have been identified by staining with silver chloride when separating 25–50 g protein. Silver staining can detect picogram levels of proteins (Guevara et al., 1982). Evaluating protein profiles before and after immunodepletion will likely enhance the chance of detecting unique protein spots. In addition to affinity columns for immunodepletion of serum proteins and human albumin, affinity columns for PSA, PAP, PSP, and TURP-27 have also been prepared using antiserum coupled to CNBr-activated Sepharose 4B (Pharmacia, Dermer et al., 1982). These are for use in a tandem fashion to remove as many common and "unwanted" proteins as possible in order to enhance the detection of unique proteins. A second advantage of immunosubtraction is that since a number of proteins have been depleted from the specimen, higher protein concentrations can be separated without distorting electrophoretic separation.

EXAMPLE VIII

IDENTIFICATION OF A BPH-SPECIFIC MARKER IN BIOLOGICAL FLUIDS

This example concerns the identification of a biomarker that is specific for, or highly restricted to, BPH and that is present within serum, urine or seminal plasma (semen). Such a marker may be identified using studies designed to identify molecules that are secreted, or shed, into body fluids.

For the identification of a BPH marker present in biological fluids, seminal plasma and prostate fluid from patients with BPH will be employed. The reason for selecting seminal plasma and prostate fluid is based on two premises: First, it is proposed that the pathophysiology of secreted or shed biomarkers for benign and malignant disease is different. For a biomarker such as PSA to reach abnormal levels in the serum, the basement membrane and stromal elements must be breached for entry into the capillary bed. It is further proposed that a destructive process does not occur in BPH, and that abnormal serum PSA levels in BPH 0are largely the result of excess production and inefficient ductal drainage with leakage into the capillary bed. For BPH, the most likely exit of secreted or shed biomarkers is via the lumen of the ducts (prostate fluid) and into the urethra. Thus prostatic fluid and seminal plasma would most likely contain a secreted BPH biomarker in the highest concentration. Second, seminal plasma and prostatic fluid, especially the latter, would have little or no contaminating molecules from other normal or abnormal processes of the urological system or other organ systems that might interfere with the search for the BPH biomarker.

To identify a BPH biomarker in seminal plasma/prostate fluid, three different approaches may be used. All three approaches are designed to enrich the chances of identifying novel BPH molecules in seminal plasma and prostate fluid.

Secreted BPH proteins may be identified by 2-D gel electrophoresis, as set forth in Example VII. Prostate fluid/ seminal plasma from normal age-matched donors, BPH, prostatitis and prostate cancer patients are separated by 2-D electrophoresis, before and after immuodepletion, and the silver-stained or Western blotted 2-D protein profiles analyzed with a computer-based image system. Protein spots identified as unique for BPH are electroeluted from preparative gels and used to immunize mice for production of MAbs.

BPH marker proteins that are secreted may also be identified by subtraction hybridization, as set forth in Example VI. This approach is used to identify mRNA transcripts that are characteristic of the BPH phenotype. To detect mRNAs differentially expressed in BPH, and not in normal or malignant prostate, a subtracted cDNA library is differentially screened with BPH, CaP and normal cDNA probes. BPH specific or enriched cDNAs are identified by Northern blot analysis and expressed as recombinant proteins. Polyclonal antisera prepared to the recombinant proteins are used to screen BPH seminal plasma to identify the secreted/shed proteins by 2-D electrophoresis. BPH specific or novel recombinant proteins are selected and used to produce MAbs.

The type of immunotolerance/immunosuppression study employed to generate BP52 (Example I) may also be used to identify secreted or shed PBH markers. Mice are rendered tolerant to semen antigens from normal donors and patients with CaP, using either active or passive induced immunosuppression, followed by immunization with the composition against which it is desired that antibodies be generated. In this case, it is important that BPH seminal plasma and/or prostate fluid immunogens be employed as the immunogens.

EXAMPLE IX

IMMUNOASSAYS TO DETECT BPH-SPECIFIC MARKERS IN FLUID SAMPLES

Following the generation of an antibody that recognizes a specific, secreted BPH biomarker, the antibody will be used to develop a sensitive two-site immunoradiometric assay (IRMA) to measure and quantitate the BPH biomarker in serum, urine and seminal plasma. Specimens from healthy male donors, patients with BPH, chronic abacterial prostatitis, CaP and a variety of non-prostate disorders will be tested to confirm the clinical utility of the immunoassay.

The development of such a reliable, reproducible, sensitive and quantitative 2-site IRMA will utilize the methods of (Huang et al., 1992; Huang et al., 1993). Briefly, affinity purified MAb will be covalently attached to 5/16-in diameter polystyrene beads to serve as the "catcher" antibody, the beads incubated with the test specimen or standard BPH antigen (i.e., BPH seminal plasma), washed and $^{125}$I-labeled MAb ("tracer" MAb) added to each bead. The "tracer" antibody may be against the same or different antigenic determinant. The beads again incubated, washed and counted in a gamma counter. The amount of antigen, in arbitrary units/ml, will be determined from a standard dose-response curve.

Such an assay is contemplated to be able to effectively and reproducibly discriminate BPH from prostatitis and CaP. To confirm this, 25–50 specimens in each of the following categories will be tested: (Berry et al., 1984) Normal donors under the age of 40, (Vital and Health Statistics, 1986) normal age-matched donors (normal rectal exam, normal PSA); (Carter & Coffey, 1990) BPH (pathology confirmed); (Mebust et al., 1989) prostatitis (all types); (Bureau of Data Management and Strategy, 1988) prostate cancer (pretreatment, all Stages and Grades); and (Issacs, 1990) prostate cancer (post-treatment, all Stages and Grades). The BPH test group will include patients on Proscar. A biomarker whose synthesis is not regulated by androgens will be required to monitor such therapy in BPH patients. Biomarker levels between the various subject categories will be compared as to range of biomarker levels, mean levels, standard deviation and standard error of the mean. From these data a cutoff value will be estimated to confirm that the BPH biomarker differentiates BPH from the other test groups.

Next, measurement of the biomarker in serum and urine will be undertaken. In addition to the subject categories outlined above, serum and urine from patients with other urogenital disorders, i.e., bladder cancer, renal cancer, kidney stones, and non-urogenital disorders will be included in this study. The first 10 ml of a urine void (i.e., urethral urine) from at least 5 individuals in these different categories will be tested. Urethral urine should contain the highest biomarker concentration and, therefore, this urine should confirm that the BPH biomarker can be detected in urine. 24 hour voids will be collected and 10 ml aliquots tested to provide the most reproducible and reliable biomarker concentrations. Biomarker levels in all categories will be compared with marker levels in the BPH specimens.

The immunoassay would be fine tuned and used to clinically diagnose the onset and progression of BPH and to monitor the disease during therapy. Such studies would involve purification of the BPH biomarker to use as a standard antigen source and for producing second generation antibodies (if needed to enhance the sensitivity of the assay). Single point samples from patients with BPH, prostatitis and cancer would be evaluated to establish baseline values for distinguishing BPH from other prostate diseases. Serial samples from BPH patients would be tested to determine if the assay can quantitate disease progression and effectively measure responses to therapy, especially hormone ablation therapies that affect the production of PSA. From the data obtained from these studies, a long-term study in aging males would be conducted to determine if the assay can detect early onset of BPH.

A cell line as described herein has been deposited with the American Type Culture Collection, 12301 Parklawn Drive, Rockville, Md., 20852 USA; and been assigned accession number ATCC No. HB 11593. The invention described and claimed herein is not to be limited in scope by the cell lines deposited since the deposited embodiment is intended as an illustration of one aspect of the invention and any equivalent cell lines which produce functionally equivalent monoclonal antibodies are within the scope of this invention. Indeed, all of the compositions and methods disclosed and claimed herein can be made and executed without undue experimentation in light of the present disclosure.

Therefore, while the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abrahamsson, P-A., Alumets, J., Wadstrom, L. B., Falkmer, S., and Grimelius, L. Peptide hormones, serotonin, and other cell differentiation markers in benign hyperplasia and in carcinoma of the prostate. In Prostate Cancer Part A: Research, Endocrine Treatment, and Histopathology, Alan R. List, Inc, 1988, pp 489–502.

Abrahamsson, P.-A., Lija, H, Falkmer, S., and Wadstrom, L. B. Immunohistochemical distribution of the three predominant secretory proteins in the parenchyma of hyperplastic and neoplastic prostate glands. The Prostate 12:39–46, 1988.

AL-Hilaly, E. S., Seddek, M. N., Basta, M. T., Shaaban, A., El-Baz, M., El-Masry, S., Al-Hilaly, E. S., and Ghoneim, M. A. Cytokeratin shedding in urine as a biological marker for bladder cancer: Monoclonal antibody-based evaluation. British J. Urol. 61:116–121, 1991.

Anderson, K. M., Baranowski, J., Bonomi, P., and Economou, S. G. Qualitative analysis of coomassie-blue-stained proteins from normal prostate, benign prostatic hypertrophy, or adenocarcinoma of the prostate, separated by two-dimensional protein electrophoresis. The Prostate 6:315–323, 1985.

Antibodies: A Laboratory Manual, E. Howell and D. Lane, Eds., Cold Spring Harbor Laboratory, (1988).

Beckett, M. L., Lipford, G. B., Haley, C. L., Schellhammer, P. F., and Wright, Jr., G. L. Monoclonal antibody PD41 recognizes an antigen restricted to prostate adenocarcinomas. Cancer Res. 51:1326–1333, 1991.

Berry, S. J., Coffey, D. S., Walsh, P. C., and Ewing, L. L. The development of human benign prostatic hyperplasia with age. J. Urol. 132:474–79, 1984.

Bosch, R. J. L. H. Pathogenesis of benign prostatic hyperplasia. Eur. Urol. 20 (suppl.2):27–30, 1991.

Bostwick, D. G, and Brawer, M. K. Prostatic intraepithelial neoplasia and early invasion in prostatic cancer. Cancer 59:788–794, 1987.

Brawer, M. K., Peehl, 'D. M., Stamey, T. A., and Bostwick, D. G. Keratin immunoreactivity in the benign and neoplastic human prostate. Cancer Res. 45:3663–3667, 1985.

Campbell, 1984, in Monoclonal Antibody Technology, Laboratory Techniques in Biochemistry and Molecular Biology Vol. 13, Burden and Von Knippenberg, Eds., Amsterdam, Elseview, 1984.

Carter, H. B., and Coffey, D. S. The prostate: An increasing medical problem. The Prostate 16:39–42, 1990.

Carter, D. B., Timmins, J. G., Adams, L. D., Lewis, R. W., Karr, J. P., Resnick, M. I., and Buhl, A. E. The antigenic relatedness of proteins from human and simian prostate fluid. The Prostate 6:395–402, 1985.

Cold Spring Harbor Laboratory Manual for Hybridoma Development.

Conry, R. M., LoBuglio, A. F., Kantor, J., Schlom, J., Loechel, F. Moore, S. E., Sumerel, L. A., Barlow, D. L., Abrams, S., and Curiel, D. T. Immune response to a carcinoembryonic antigen polynucleotide vaccine. Cancer Res. 54:1164–1168, 1994.

Cox, Graham J. M., Zamb, Tim J., and Babiuk, Lorne A., Bovine Herpesvirus 1: Immune Responses in Mice and Cattle Injected with Plasmid DNA. Journal of Virology 67:(9)5664–5667, 1993.

Dalton, D. L. Elevated serum prostate-specific antigen due to acute bacterial prostatitis. Urology 33:465–467, 1989.

Dermer, G. B., Silverman, L. M., and Chapman, J. F. Enhancement techniques for detecting trace and fluid-specific components in two-dimensional electrophoresis patterns. Clin. Chem. 28:759–765, 1982

DeVere White, R. W., Meyers, F. J., Soares, S. E., Miller, D. G., and Soriano, T. F. Urinary prostate specific antigen levels: Role in monitoring the response of prostate cancer to therapy. J. Urol. 147:947–951, 1992.

Dillman, R. O., et al. (1988) Antibody, Immunocon. Radiopharm., 1:65–77.

Edwards, J. J., Tollaksen, S. L., and Anderson, N. G. Proteins of human semen. I. Two-dimensional mapping of human seminal fluid. Clin. Chem. 27:1335–1340, 1981.

Edwards, J. J., Anderson, N. G., Tollaksen, S. L., von Eschenbach, A. C., and Guevara, Jr., J. Proteins of human urine. II. Identification by two-dimensional electrophoresis of a new candidate marker for prostate cancer. Clin. Chem. 28:160–163, 1982.

Fynan, Ellen F., Webster, Robert G., Fuller, Deborah H., Haynes, Joel R., Santoro, Joseph C., and Robinson, Harriet L. DNA vaccines: Protective immunizations by parenteral, mucosal, and gene-gun inoculations. Proc. Natl. Acad. Sci. USA, 90:11478–11482, 1993.

Fiorelli, G., De-Bellis, A., Longo, A., Pioli, P., Costantini, A., Giannini, S, Forti, G., and Serio, M. Growth factors in the human prostate. J. Steroid Biochem Mol Biol. 40:199–205, 1991.

Frenette, G., Tremblay, R. R., and Dube, J. Y. Variations in 3H-diisopropylfluorophosphate binding proteins in human seminal plasma. Int. J. Androl. 14:186–195, 1991.

Gefter et al., Somatic Cell Genet. 3:231–236 1977.

Gerhardt, P., Mevag, B., Ruie, H., Tveter, K. J., and Purvis, K. Two-dimensional electrophoresis of proteins from different lobes of the rat prostate and seminal vesicle. The Prostate 7:321–326, 1985.

Ghose, et al. (1982) Meth. Enzymology, 93:280–333.

Goding, 1986, in Monoclonal Antibodies: Principles and Practice, 2d Ed., Orlando, Fla., Academic Press, 1986.

Graham, CW., Lynch, J. H., and Djakiew, D. Distribution of nerve growth factor-like protein and nerve growth factor receptor in human benign prostatic hyperplasia and prostatic adenocarcinoma. J. Urol. 147:1444–1447, 1992.

Grayhack, J. T., Wendel, E. F., Oliver, L., and Lee, C. Analysis of specific proteins in prostatic fluid for detecting prostatic malignancy. J. Urol. 121:295–299, 1979.

Guevara, Jr., J., Johnston, D. A., ramagall, LoSo, Martin, B. A., Capetillo, S., and Rodriguez, L. V. Quantitative aspects of silver deposition in proteins resolved in complex polyacrylamide gels. Electrophoresis 3:197–205, 1982.

Health Care Financing Administration, Bureau of Data Management and Strategy: Prospective Payment System Monitoring Report Tables 1986. U.S. Department of Health and Human Services, 1988.

Horoszewicz, J. S., Kawinski, E., and Murphy, G. P. Monoclonal antibodies to a new antigenic marker in epithelial prostate cells and serum of prostatic cancer patients. Anticancer Res. 7:927–936, 1987.

Huang, C-L., Brassil, D., Rozzell, M., Schellhammer, P. F., and Wright, G. L., Jr. Comparison of prostate secretory protein with prostate specific antigen and prostate acid phosphatase as a serum biomarker for diagnosis and monitoring patients with prostate carcinoma. The Prostate 23:201–212, 1993.

Hughes, M., Sehgal, A., Hadman, M., and Bos, T. J. Heterodimerization with c-Fos is not required for cell transformation of chicken embryo fibroblasts by Jun. Cell Growth and Differentiation 3:889–897, 1992.

Ibrahim, G. K., Kerns, B-J. M., MacDonald, J. A., Ibrahim, S. N., Kinney, R. B., Humphrey, P. A., and Robertson, C. N. Differential immunoreactivity of epidermal growth factor in benign, dysplastic and malignant prostatic tissues. J. Urol. 149:170–173, 1993.

Issacs, J.T. Importance of the natural history of benign prostatic hyperplasia in the evaluation of pharmacologic intervention. The Prostate Suppl 3: 1–7, 1990.

Johnson, A. H., Merchant, D. J., Lee, C., Norman, J., and Bourgeois, N. A search for differentiation markers in prostatic fluid components with two-dimensional electrophoresis and multiple protein detectors. The Prostate 7:429–439, 1985.

Kantor, J., Irvine, K., Abrams, S., Kaufman, H., DiPietro, J., and Schlom, J. Antitumor activity and immune responses induced by a recombinant CEA-vaccinia virus vaccine. J. Natl. Cancer Inst. 84:1084–1091, 1992.

Kimura, S., et al. (1983) Immunogenetics, 11:373–381.

Kohler and Milstein, Nature 256:495–497, 1975

Kohler and Milstein, Eur. J. Immunol. 6:511–519, 1976

Kumar, V. L., Wadhwa, S. N., Kumar, V., and Farooq, A. Androgen, estrogen, and progesterone receptor contents and serum hormone profiles in patients with benign hypertrophy and carcinoma of the prostate. J. Surg. Oncol. 44:122–128, 1990.

Lawson, R. K. Benign prostatic hyperplasia and growth factors. Urology 29:5–7,1990.

Lee, C., Sherwood, E. R., Sensibar, J. A., Berg, L. A., Chen, Y. C., and Tseng, C. C. Profile matching and profile subtraction: Application of computer-based image analysis system for two-dimensional electrophoresis gels. Biotechniques 7:374–377, 1989.

Lee, C., Hu, S.-E., Lok, M. S., Chen, Y. C., and Tseng, C. C. Microcomputer-based image analysis systems for two-dimensional electrophoresis gels. Biotechniques 6:216–224,1988.

Lee, C., Tsai, Y., Sensibar, J., Oliver, L, and Grayhack, J. T. Two-dimensional characterization of prostatic acid phosphatase, prostatic specific antigen and prostate binding protein in expressed prostatic fluid. The Prostate 9:135–146, 1986.

Lilja, H., and Abrahamsson, P.-A. Three predominant proteins secreted by the human prostate gland. The Prostate 12:29–38, 1988.

Lloyd, S. N., Brown, I. L., and Leake, R. E. Transforming growth factor-alpha expression in benign and malignant human prostatic disease. Int. J. Biol. Markers 7:27–34, 1992.

Lokeshwar, B. L., and Block, N. L. Isolation of a prostate carcinoma cell proliferation-inhibiting factor from human seminal plasma and its similarity to transforming growth factor beta. Cancer Res. 52:5821–5825, 1992.

McNeal, J. E., Price, H. M., Redwine, E. A. et al. Stage A versus stage B adenocarcinoma of the prostate: Morphological comparison and biological significance. J. Urol. 139:61–65, 1988.

Matthew, W. D., and Sandrock, Jr., A. W. Cyclophosphamide treatment used to manipulate the immune response for the production of monoclonal antibodies. J. Immunol. Methods 100:73–82, 1987.

Matzkin, H., and Soloway, M. S. Immunohistochemical evidence of the existence and localization of aromatase in human prostatic tissues. The Prostate 21:309–314, 1992.

Maygarden, S. J., Strom, S., and Ware, J. L. Localization of epidermal growth factor receptor by immunohistochemical methods in human prostatic carcinoma, prostatic intraepithelial neoplasia, and benign hyperplasia. Arch Pathol Lab Med. 116:269–273, 1992.

Mebust, W. K., Holtgrewe, H. L, Cockett, A. T. K., and Peters, P. C. Writing Committee. Transurethral prostatectomy: Immediate and postoperative complications. A cooperative study of 13 participating institutions evaluating 3,885 patients. J. Urol. 141:243–247, 1989.

Mellon, K., Thompson, S., Charlton, R. C., Marsh, C., Robinson, M., Lane, D. P., Harris, A. L., Wilson Horne, C. H., and Neal, D. E. p53, c-erbB-2 and the epidermal growth factor receptor in the benign and malignant prostate. J. Urol. 147:496–499, 1992.

Mori, H., Maki, M., Oishi, K., Jaye, M., Igarashi, K., Yoshida, 0., and Hatanaka, M. Increase expression of genes for basic fibroblast growth factor and transforming growth factor type beta 2 in human benign prostatic hyperplasia. The Prostate 16:71–80, 1990.

Nakamoto, T., Chang, C., Li, A., and Chodak, G. W. Basic fibroblast growth factor in huan prostate cancer cells. Cancer Res. 52:571–577, 1992.

Nakamura, R. M., Voller, A. and Bidwell, D. E., Enzyme immunoassays: heterogeneous and homogeneous systems, Chapter 27.

National Center for Health Statistics: Vital and Health Statistics. Series 13, No. 96. Utilization of Short Stay Hospitals, United States, 1986 Annual Summary. Washington D.C.: Public Health Service, 1988. DHHS Publication No. (PHS) 88–1757.

O'Brien, W. M., and Lynch, J. H. Hydroxyproline as a marker for following patients with metastatic prostate cancer. J. Urol. 139:66–68, 1988.

Pagano, F., Zattoni, F., Vianello, F., Piazza, R., and Capitanio, G. Is there a relationship between benign prostatic hyperplasia and prostate cancer? Eur. Urol. 20 (suppl 2): 31–35, 1991.

Partin, A. W., Getzenberg, R. H., CarMichael, M. J., Vindivich, D., Yoo, J., Espstein, J. I., and Coffey, D. S. Nuclear matrix protein patterns in human benign prostatic hyperplasia and prostate cancer. Cancer Res. 53:744–746, 1993.

Pietersz, G. A., et al. (1988) Antibody, Immunoconj. Radiopharm., 1:79–103.

Rackley, R. R., Yang, B., Pretlow, T. G., Absul-Karim, F. W., Lewis, T. J., McNamara, N., Delmoro, C. M., Bradley, E. L., Jr., Kursh, E., and Resnick, M. I. Differences in the leucine aminopeptidase activity in extracts from human prostatic carcinoma and benign prostatic hyperplasia. Cancer 68:587–593, 1991.

Radovich, J., and Talnage, D. W. Antigenic competition: Cellular or humoral. Science 158:512–514, 1967.

Sambrook et al. (1989). Molecular cloning: A laboratory manual. Cold Spring Harbor Laboratory. Cold Spring Harbor, N.Y.

Shah, G. V., Noble, M. J., Austenfeld, M., Weigel, J., Deftos, L. J., and Mebust, W. K. Presence of calcitonin-like immunoreactivity (iCT) in human prostate gland: evidence for iCT secretion by cultured prostate cells. The Prostate 21:87–97, 1992.

Shaikh, N., Lai, L, McLoughlin, J., Clark, D., and Williams, G. Quantitative analysis of epidermal growth factor in human benign prostatic hyperplasia and prostatic carcinoma and its prognostic significance. Anticancer Res. 10:873–874, 1990.

Sherwood, E. R., Fong, C-J., Lee, C., and Kozlowski, J. M. Basic fibroblast growth factor: A potential mediator of stromal growth in the human prostate. Endocrinology 130:2955–2963, 1992.

Sherwood, E. R., Theyer, G., Steiner, G., Berg, L. A., Kozlowski, J. M., and Lee, C. Differential expression of specific cytokeratin polypeptides in the basal and luminal epithelia of the human prostate. The Prostate 18:303–314, 1991.

Stearns, M. E., and Wang, M. Type IV collagenase (Mr 72,000) expression in human prostate: Benign and malignant tissue. Cancer Res. 53:878–883, 1993.

Tanaka, M., Sasaki, H., Kino, I., Sugimura, T., and Terada, M. Genes preferentially expressed in embryo stomach are predominantly expressed in gastric cancer. Cancer Res. 52:3372–3377, 1992.

Tang, De-chu, DeVit, Michael and Johnston, Stephen A., Genetic immunization is a simple method for eliciting an immune response, Nature, 356:152–154, 1992.

Teni, T. R., Sheth, A. R., Kamath, M. R., and Sheth, N. A. Serum and urinary prostatic inhibin-like peptide in benign prostatic hyperplasia and carcinoma of prostate. Cancer Lett. 43:9–14, 1988.

Theyer, G., Kramer, G., Assmann, I., Sherwood, E., Preinfalk, W., Marberger, M., Zechner, O, and Steiner, G. E. Phenotypic characterization of infiltrating leukocytes in benign prostatic hyperplasia. Lab. Invest. 66:96–107, 1992.

Tremblay, J., Frenette, G., Tremblay, R. R., Dupont, A., Thabet, M., and Dube, J. Y. Excretion of three major prostatic secretory proteins in the urine of normal men and patients with benign prostatic hypertrophy or prostate cancer. The Prostate 10:235–243, 1987.

Tsai, Y. C., Harrison, H. H., Lee, C., Daufeldt, J. A., Oliver, L., and Grayhack, J. T. Systematic characterization of human prostatic fluid proteins with two-dimensional electrophoresis. Clin. Chem. 30:2026–2030, 1984.

Uchijima, Y., Yoshida, K., and Saitoh, H. Significance of prostatic acid phosphatase, gamma-seminoprotein and prostatic specific antigen in the urine. Hinyokika Kiyo 37:1255–60, 1991.

Ulmer, J. B., Donnelly, J. J., Parker, S. E., Rhodes, G. H., Felgner, P. L., Dwarke, V. J., Gromkowski, S. H., Deck, R. R., DeWitt, C. M., Friedman, A. Hawe, L. A., Leander, K. R., Martinez, D. Perry, H. C., Shiver, J. W., Montgomery, D. L., Liu, M. A., Heterologous Protection Against Influenza by Injection of DNA Encoding a Viral Protein, Science, 259:1745–1749, 1993.

Vaickus, L., et al. (1991) Cancer Invest., 9:195–209.

van-Dieijen-Visser, M. P., Hendriks, M. W., Delaere, K. P., Gijzen, A. H., and Brombacher, P. J. The diagnostic value of urinary transferrin compared to serum prostatic specific antigen (PSA) and prostatic acid phosphatase (PAP) in patients with prostatic cancer. Clin. Chim. Acta. 177:77–80, 1988.

Verhagen, A. P. M., Ramaekers, C. S., Aalders, T. W., Schaafsma, H. E., Debruyne, F. M. J., and Schalken, J. A. Colocalization of basal and luminal cell-type cytokeratins in human prostate cancer. Cancer Res. 52:6182–6187, 1992.

Wada, F., Nishi, N., Tanaka, Y., Muguruma, Y., Tanaka, K., Usami, M., Kotake, To, Matsui, S.-I., Sandberg, A. A., and Matuo, Y. Comparison of subcellular proteins of normal prostate, benign prostatic hypertrophy, and prostatic cancer: Presence of BPH-associated nonhistone proteins. The Prostate 7:107–115, 1985.

Wang, Bin, Ugen, Kenneth E., Srikantan, Vasantha, Agadjanyan, Michael G., Dang, Kesen, Refaeli, Yosef, Sato, Alice L., Boyer, Jean, Williams, William V., and Weiner, David B., Gene inoculation generates immune responses against human immunodeficiency virus type 1, Proc. Natl. Acad. Sci. USA, 90:4156–4160, 1993.

Whitton, J. Lindsay, Sheng, Ning, Oldstone, Michael B. A., and McKee, Tom A., A "String-of-Beads" Vaccine, Comprising Linked Minigenes, Confers Protection from Lethal-Dose Virus Challenge, Journal of Virology, 67:(1) 348–352,1993.

Yang, Y., Chisholm, G. D., and Habib, F. K. The distribution of PSA, cathepsin-D, and pS2 in BPH and cancer of the prostate. The Prostate 21:201–208, 1992.

What is claimed is:

1. An antibody having immunospecificity for the antigen recognized by the monoclonal antibody BP52.

2. The antibody of claim 1, wherein the antibody is a polyclonal antibody.

3. The antibody of claim 1, wherein the antibody is a monoclonal antibody.

4. The antibody of claim 3, wherein the antibody is the monoclonal antibody BP52 produced by the hybridoma ATCC HB 11593.

5. The antibody of claim 1, wherein the antibody is linked to a detectable label.

6. The antibody of claim 5, wherein the antibody is linked to a radioactive label, a flurogenic label, a nuclear magnetic spin resonance label or biotin.

7. The antibody of claim 5, wherein the antibody is linked to an enzyme that will generate a colored product upon contact with a chromogenic substrate.

8. The antibody of claim 1, wherein the antibody is further defined as an Fv fragment, an F(ab')$_2$ fragment or an Fab fragment.

9. A hybridoma that produces a monoclonal antibody having immunospecificity for the antigen recognized by the monoclonal antibody BP52.

10. The hybridoma of claim 9, wherein the hybridoma is ATCC HB 11593.

11. An antibody immunoreactive with the antigen recognized by the monoclonal antibody BP52, preparable by obtaining the antigen, and immunizing an animal with an amount of the antigen effective to stimulate the production of the antibody immunoreactive with the antigen.

12. The antibody of claim 11, wherein the BP52 antigen is obtained by comparative two dimensional gel electrophoresis.

* * * * *